(12) United States Patent
Njemanze

(10) Patent No.: US 7,318,834 B2
(45) Date of Patent: Jan. 15, 2008

(54) APPARATUS AND METHOD FOR HYPOTHERMIA AND REWARMING BY ALTERING THE TEMPERATURE OF THE CEREBROSPINAL FLUID IN THE BRAIN

(76) Inventor: Philip Chidi Njemanze, No 1 Uratta/MCC Road, Owerri, Imo, P.O. Box 302 (NG)

( * ) Notice: Subject to any disclaimer, the term of this patent is extended or adjusted under 35 U.S.C. 154(b) by 0 days.

(21) Appl. No.: 10/773,144

(22) Filed: Feb. 9, 2004

(65) Prior Publication Data

US 2005/0177212 A1    Aug. 11, 2005

(51) Int. Cl.
*A61F 7/12* (2006.01)
(52) U.S. Cl. ..................................... 607/105
(58) Field of Classification Search ............ 607/96, 607/101–107, 113–114
See application file for complete search history.

(56) References Cited

U.S. PATENT DOCUMENTS

| | | | |
|---|---|---|---|
| 6,217,552 B1 * | 4/2001 | Barbut et al. ............... | 604/113 |
| 6,660,026 B2 * | 12/2003 | Larnard et al. ............. | 607/104 |
| 6,929,656 B1 * | 8/2005 | Lennox ...................... | 607/105 |
| 7,004,961 B2 * | 2/2006 | Wong et al. ................ | 607/105 |
| 7,144,418 B1 * | 12/2006 | Lennox ...................... | 607/105 |
| 2002/0198579 A1 * | 12/2002 | Khanna ...................... | 607/105 |
| 2004/0143312 A1 * | 7/2004 | Samson et al. ............. | 607/105 |

\* cited by examiner

Primary Examiner—Roy D. Gibson

(57) ABSTRACT

The invention relates to a method for hypothermia and rewarming of the cerebrospinal fluid in the brain. In one embodiment, cooling and rewarming of the cerebrospinal fluid is accomplished by applying cooling and rewarming elements externally placed in contact with the skin overlying the cerebrospinal fluid cisterns at the back of the head and spine regions of a patient. In another embodiment, hypothermia and rewarming is accomplished using a double barrel ventricular catheter placed within the lateral ventricles with one catheter used for heat exchange and the other for drainage of excess cerebrospinal fluid. In yet another embodiment of the invention, hypothermia and rewarming is accomplished using a loop catheter with fluid running through the loop placed in the lateral ventricles.

20 Claims, 21 Drawing Sheets

APPARATUS AND METHOD FOR HYPOTHERMIA AND REWARMING BY ALTERING THE TEMPERATURE OF THE CEREBROSPINAL FLUID IN THE BRAIN

CROSS-REFERENCE TO RELATED APPLICATION

U.S. PATENT DOCUMENTS

| 4572188 | February, 1986 | Augustine et al. | 128/380 |
|---|---|---|---|
| 5405371 | April, 1995 | Augustine et al. | 607/107 |
| 5486208 | January, 1996 | Ginsburg | 607/106 |
| 5916242 | June, 1999 | Schwatz | 607/113 |
| 6126680 | October, 2000 | Wass | 607/96 |
| 6197045 | March, 2001 | Carson | 607/104 |
| 6547811 | April, 2003 | Becker et al. | 607/105 |
| 6558412 | May, 2003 | Dobak, III. | 607/105 |
| 6581400 | June, 2003 | Augustine et al. | 62/259.3 |
| 6620187 | September, 2003 | Carson et al. | 607/104 |
| 6622725 | September, 2003 | Fisher et al. | 128/204.21 |

STATEMENT REGARDING FEDERALLY SPONSORED RESEARCH OR DEVELOPMENT

Not applicable

REFERENCE TO MICROFICHE APPENDIX

Not applicable

BACKGROUND OF THE INVENTION

The present invention generally relates to the selective modification and control of a patient's body temperature, specifically to the altering of the temperature of the cerebrospinal fluid that circulates within the brain.

Hypothermia is a clinical condition of abnormally low body temperature generally characterized by a core body temperature of 35 degrees Celcius or less. By severity, mild hypothermia describes a body core temperature within the range of 32 degrees Celcius to 35 degrees Celcius, moderate between 30 degrees Celcius to 32 degrees Celcius, severe between 24 degrees Celcius to 30 degrees Celcius, and profound—a body temperature of less than 24 degrees Celcius. These are relative distinctions and definition may vary widely in literature. However, in severe hypoxic-ischemic injury, animal models suggest that the optimum temperature is between 32 degrees Celcius and 34 degrees Celcius as disclosed in an article by Colbourne F, Sutherland G, Corbett D., entitled "Posttraumatic hypothermia: a critical appraisal with implication for clinical treatment", published in Mol Neurobiol, vol. 14, pp. 171-201 (1997). As body temperature falls below 34 degrees Celcius, there is an increased risk of infection, coagulopathy, thrombocytopenia, renal impairment, and pancreatitis as disclosed by Schubert A, in an article entitled "Side effects of mild hypothermia", published in J Neurosurg Anesthes vol. 7, pp. 139-147 (1995); and also by Metz C, Holzschuh M, Bein T, et al., in an article entitled "Moderate hypothermia in patients with severe head injury: cerebral and extracerebral effects", published in J. Neurosurg., vol. 85, pp. 533-541 (1996).

To be effective, hypothermia needs to be achieved within 2-6 hours of severe hypoxic-ischemic injury possibly begun in the ambulance as disclosed in an article by Bernard S A, Gray T W, Buist M D, et al., entitled "Treatment of comatose survivors of out-of-hospital cardiac arrest with induced hypothermia", published in N Engl J. Med., vol. 346, pp. 557-563 (2002). The duration of hypothermia for hypoxic-ischemic injury depends on the severity of the injury and the delay before the hypothermia is achieved. Within limits, a more severe injury or a longer delay can be compensated for by cooling for longer as disclosed in an article by Gunn A J, entitled "Cerebral hypothermia for prevention of brain injury following perinatal asphyxia", published in the Curr Opin Pediatr vol. 12, pp. 111-115 (2000). What is therefore required is a device that will achieve hypothermia in the shortest possible time.

Conversely, hyperthermia is a clinical condition of abnormally high body temperature, due to exposure to a hot environment or surroundings, overexertion, or fever. Body core temperatures may range from 38 degrees Celcius to 41 degrees Celcius due to conditions such as fever, and may be substantially higher in cases of exposure and overexertion. Hyperthermia is a serious and potentially fatal condition. The common causes of hyperthermia are systemic inflammatory response, sepsis, stroke, or other brain injury. The mechanisms of the effect of hyperthermia on the brain remains to be fully elucidated, however, there is evidence to indicate that even mild increases in temperature may contribute to neurological deficits. Hyperthermia also increases the cerebral metabolic rate and may deplete cell energy stores. Following hypothermia there is rewarming to normal body temperature.

Induced hypothermia has been used clinically for neuroprotection during cardiovascular surgery, severe cardiac conditions (cardiac arrest, myocardial infarction), neurosurgery, head trauma, subarachnoid hemorrhage, spinal trauma, stroke, thoracic aortic aneurysm repair, and liver transplantation. The mechanisms of action of clinical hypothermia may include blunting of post-insult release of neurotransmitters such as glutamate, reduction of cerebral metabolic rate, moderation of intracellular calcium, prevention of intracellular protein synthesis inhibition, and reduction of free radical formation as well as other enzymatic cascades and even genetic responses. For example, it has been demonstrated that hypothermia produces an attenuation of the release of excitatory neurotransmitters in meningitis and suggest that this treatment may attenuate neuronal stress as disclosed by Irazuzta J E, Olson J, Kiefaber M P, Wong H., in an article entitled "Hypothermia decreases excitatory neurotransmitter release in bacterial meningitis in rabbits", published in Brain Res., vol. 847, pp. 143-148 (1999).

In the clinical setting, methods of induced hypothermia could be classified as whole body and regional hypothermia, invasive and noninvasive methods. Whole body hypothermia is usually invasive, not only takes a significant amount of time, but also subjects the patient to deleterious effects of hypothermia including cardiac arrhythmias, coagulation problems, increased susceptibility to infections, and problems of discomfort such as profound shivering. One way to induce whole body hypothermia is to externally cool the blood and pump it back to the patient using a bypass machine. This method is an extremely invasive procedure that subjects vast quantities of the patients' blood to pumping for an extended length of time. Such external pumping of blood may be harmful to the blood, and continued pumping of blood into a patient for extensive periods of time, for example, more than one or two hours, is generally avoided. During such procedures anticoagulants for example, heparin may be used, to prevent clotting which may present other undesirable consequences in victims of cerebrovascular accidents.

Other means of inducing hypothermia which do not require external pumping including the use of catheter has been proposed. For example, U.S. Pat. No. 5,486,208, to Ginsburg, describes a catheter that is inserted into a blood vessel and a portion of the catheter heated or cooled, transferring heat to the patient's blood and thereby affecting the overall body temperature of the patient. One clear advantage of such devices and methods is that, they may avoid the problems associated with external pumping of blood, however, the method is still invasive and do not eliminate the difficulties that arise when the entire body is subjected to hypothermia.

Variations of balloons capable of acting as ongoing heat transfer balloons by the continual flow of heat transfer medium through the balloon have also been introduced. U.S. Pat. No. 6,558,412 to Dobak III, describes a flexible catheter that is inserted through the vascular system of a patient to place the distal tip of the catheter in an artery feeding the selected organ. A compressed refrigerant is pumped through the catheter to an expansion element near the distal tip of the catheter, where the refrigerant vaporizes and expands to cool a flexible heat transfer element in the distal tip of the catheter. The heat transfer element cools the blood flowing through the artery, to cool the selected organ, distal to the tip of the catheter.

There have been attempts to achieve regional cerebral hypothermia, by directly cooling the surface of the head. For example, by placing the head in a cooled helmet or shroud, or even injecting a cold solution into the head region. U.S. Pat. No. 6,581,400 to Augustine et al., describes an apparatus for convectively and evaporatively cooling a patient's head. The apparatus includes an upper sheet and a base sheet that are attached at a plurality of locations to form a convective device adaptable to the patient's head. Pressurized air is distributed throughout the convective device and flows to the patient's head through the apertures in the base sheet. U.S. Pat. No. 6,126,680 to Wass discloses a method and apparatus for convective cooling of the brain in which cooled air is passed over a patient's head resulting in convective cooling of the patient's brain. The convective brain cooling apparatus comprises an air-diffusing coverlet adapted to interface with an air-cooling device and a coverlet capable of surrounding the patient's head and/or neck region. The method may also include the additional step of selectively controlling cerebral blood flow and/or cerebral metabolism to further cool the brain or to maintain the brain in a hypothermic state relative to the patent's core temperature. However, the insulating qualities of the skull make it difficult to effectively lower brain core temperature, and the blood flow that may fail to provide sufficient heat transfer circulation to the brain itself when the surface of the head is cooled. Patients usually would require general anesthesia, in order to tolerate immersion or direct exposure of the head to a cold solution or cooling surface.

The use of contact pad systems such as that disclosed in U.S. Pat. No. 6,197,045, to Carson and U.S. Pat. No. 6,620,187 to Carson et al., for selectively cooling and/or heating bodily tissue is known. In such systems a fluid, e.g. water or air, is circulated through one or more pads to affect surface-to-surface thermal energy exchange with a patient. Cooling using external methods can lower the temperature of these oxygen-sensitive organs but only very slowly at rates of less than 0.05 degrees Celcius/minute (only 3 degrees Celcius/hr). In critical conditions there may be loss of pulse or inadequate perfusion, as a result core organs cools via direct tissue thermal conduction. Unfortunately, the speed of cooling with these techniques is too slow to prevent lethal outcome due to ischemic reperfusion injury to vital organs, including the heart and brain.

To overcome these limitations, U.S. Pat. No. 6,547,811 to Becker et al., provides for the application of phase-change particulate slurry cooling systems, equipment, and methods designed for cooling patients rapidly and safely. However, the '811 patent describes an invasive method for delivery of slurry for cooling of the brain. According to the '811 patent, the operator first identifies the region of the carotid artery and the jugular vein in the neck. The skin is punctured with a needle and a catheter is inserted into the pericarotid region of the soft tissue of the neck. The external portion of the catheter is attached to a syringe containing the slurry. A specified volume of slurry is then injected into the soft tissues of the neck in the vicinity of the carotid artery and the jugular vein.

Rather than cooling the brain by the relatively slow heat conduction through the low heat conductivity of the bony skull and hair covering the head, U.S. Pat. No. 5,916,242 to Schwatz describes the use of a light-weight, easily applied neck encircling collar in firm contact with the soft tissue of the neck, and particularly in good thermal contact with the carotid arteries traversing the neck. A coolant flowing through channels embedded in the collar rapidly cools the blood flowing through the carotid arteries which branch into blood vessels throughout the brain providing vascular access and attendant rapid internal cooling throughout the brain.

In view of the foregoing, it may be appreciated that medical applications of hypothermia are ever increasing. By way of example, hypothermic devices may be utilized in early therapy to reduce neurological damage incurred by stroke and head trauma patients. Additional applications include selective patient heating/cooling during surgical procedures such as cardiopulmonary bypass operations.

As these and other medical applications have evolved, the inventor has recognized the desirability of enhancing the flexibility, predictability, responsiveness, and portability of hypothermic devices. Specifically, while known heating/cooling devices have proven effective for many applications, the inventor has recognized that additional performance objectives and potential applications can be realized via the implementation of further improved thermoregulatory systems and associated methodologies based on new insights into pathophysiological mechanisms. Particularly, the inventor makes a principle departure from prior art by focusing on cooling the cerebrospinal fluid (CSF) bathing the brain centers of thermoregulation and thereby altering the central and peripheral afferents to neurons of the preoptic anterior hypothalamus and posterior hypothalamus and hence centrally resetting the body temperature to the desired level. Other design considerations include adapting the device for use in an ambulance, integrating the device with other neurointensive care procedures without increasing invasiveness of use of hypothermia in the clinical and emergency care settings.

In most cases, prior art lacks flexibility and portability and their application requires use in a controlled clinical setting. This limits their use particularly at sites of accidents by emergency rescue teams, as a result, hypothermia is usually applied much later on arrival to specialized centers with a controlled clinical environment after considerable damage has been done and efforts aimed at neuroprotection at such a late stage might be least rewarding. What is then required is a flexible and portable system easy to use during transportation of the victims from the site of the accident to the hospital.

In most instances the application of hypothermia according to the teachings of prior art requires specialized skills of the attending medical personnel or surgeon. This limits the scope of application to only selected centers in highly industrialized countries. What is therefore required is a device and method that could easily be carried out by anyone not necessarily with special skills but finds himself/herself at the scene of a road traffic accident or after a natural disaster such as after an earthquake or hurricane.

Prior art in most cases is highly invasive with serious adverse effects. The risk benefit-analyses does not permit use in many instances where application of hypothermia could have otherwise been useful. What is therefore required is a noninvasive method of hypothermia.

Prior art requires extensive expensive equipment usually requiring trained personnel. This limits availability in remote centers where there are first responders to accidents. What is therefore required is simple equipment that is affordable to remote centers.

Prior art lacks specificity in operational mechanism. Prior art focuses on cooling/heating blood or tissue surrounding major vessels. This approach is countered by the body's own mechanisms of thermoregulation and therefore is rendered ineffective or achieves very minimal effects at the brain sites of regulation even during extensive high risk whole body exposures. What is required, therefore, is a method with high specificity, acting directly at brain centers by thermal exchange with the CSF, reducing cerebral metabolic rate and improving energy stores and resetting thermoregulation.

Prior art based on cooling whole blood exposes vital organs to metabolic mismatch, between metabolic rate and optimal temperature for enzymatic and hormonal processes, as a result several enzymatic cascades are shut down which maybe vital for critical processes in the human body and hence the adverse effects. What is required is a method that centrally alters metabolic rate in synchrony with thermoregulation, such that, the body physiologically resets the level of hormonally and enzymatically dependent processes to the level of temperature permissible.

Prior art undesirably cools other vital organs such as the lungs and thereby promoting the growth of infection, as a result pneumonia is a frequent complication of hypothermia. What is required is a method that avoids undesirable cooling of other organs.

Prior art usually involves two separate phases of cooling and rewarming with elaborate distinct methods, usually requiring switching devices. What is required is a device that integrates both the cooling and rewarming phases into a simple two-step procedure without switching of apparatus.

Prior art lacks dynamic responsiveness to intensive care nursing needs considering variations in other vital signs such as mean arterial blood pressure (MABP), end-tidal partial pressure of carbon-dioxide ($PCO_2$), mean cerebral blood flow velocity (MCBFV), and intracranial pressure (ICP). As a result the level of hypothermia using prior art is not necessarily responsive to vital signs status of the patient but is decided empirically. The rationale for a dynamic responsive system is best illustrated with the hemodynamic status after head injury. In cases of head injury, ICP is the pivotal determinant of cerebral blood flow (CBF) because of its influence on the cerebral perfusion pressure (CPP) (defined as the MABP minus the ICP) as described by Aaslid R., in an article entitled "Cerebral hemodynamics", in a book by Newell D W, et al., (eds.) entitled "Transcranial Doppler", published by Raven Press, New York: p. 49 (1992). Rise in cerebral perfusion pressure within the operative range of cerebral autoregulation results in compensatory active vasoconstriction to maintain a stable cerebral blood flow. The vasoconstriction leads to a decrease in cerebral blood volume and thereby to a decrease in intracranial pressure, as described by Rosner M., in an article entitled "Pathophysiology and management of increased intracranial pressure", in a book "Neurosurgical intensive care" by Andrews B T. (ed.), published by McGraw Hill Inc., New York: pp. 57-112 (1993). Below the lower cerebral autoregulatory limit or with autoregulatory failure in some patients after head injury, an increase in cerebral perfusion pressure will result in passive vasodilatation, which will increase the cerebral blood volume and therefore the intracranial pressure. In this situation of cerebral autoregulatory failure, cerebral blood flow will vary with cerebral perfusion pressure, and a stable blood flow can no longer be maintained. An index comparing arterial blood pressure and intracranial pressure, the PRx, has been described by Czosnyka M, et al., disclosed in an article entitled "Continuous assessment of the cerebral vasomotor reactivity in head injury", published in Neurosurgery, vol. 41, pp. 11-17 (1997). PRx illustrates the correlation between arterial blood pressure and intracranial pressure. If intracranial pressure follows arterial blood pressure in a parallel fashion, there is a good correlation, and the PRx index is positive. On the other hand, if an arterial blood pressure increase causes vasoconstriction (that is, pressure autoregulation is preserved), a reduction in cerebral blood volume, and a decrease in intracranial pressure, the positive correlation will be lost; in this case the PRx will approach zero or even become negative, indicating well preserved cerebrovascular reactivity. The PRx index has been validated and it was further advocated that dynamic cerebrovascular autoregulation be measured using a moving correlation coefficient between arterial blood pressure and cerebral blood flow velocity, the Mx, as disclosed by Lang E W, Lagopoulos J, Griffith J, et al., in an article entitled "Cerebrovascular reactivity testing in head injury: the link between pressure and flow", published in J Neurol Neurosurg Psychiatry, vol. 74, pp. 1053-1059 (2003).

What is required is a system of body temperature cooling that is fully integrated with other vital signs and functions in a dynamic servo-feedback and feed-forward loop that could be used with a computerized algorithm. This will permit that the level of hypothermia is decided based on changes in vital signs status.

Prior art provides transient beneficial effects of hypothermia, which easily reverses after a comparatively short duration. Therapeutic hypothermia maintains the ICP at lower levels during the cooling phase, but once patients were rewarmed, the ICP elevated to levels of normothermic patients as disclosed by Slade J, Kerr M E, Marion D., an article entitled "Effect of therapeutic hypothermia on the incidence and treatment of intracranial hypertension", published in J Neurosci Nurs, vol. 31, pp. 264-269 (1999). Others have shown that hypothermia reliably reduced intracranial pressure as disclosed in articles by Jiang J, Yu M, Zhu C., entitled "Effect of long-term mild hypothermia therapy in patients with severe traumatic brain injury: 1-year follow-up review of 87 cases", published in J Neurosurg, vol. 93, pp. 546-549 (2000); by Shiozaki T, Hayakata T, Taneda M, et al., entitled "A multicenter prospective randomized controlled trial of the efficacy of mild hypothermia for severely head injured patients with low intracranial pressure", published in the J Neurosurg, vol. 94, pp. 50-54 (2001); by Clifton G L, Miller E R, Choi S C, et al., entitled "Lack of effect of induction of hypothermia after acute brain injury", published in N Engl J Med, vol. 344, pp. 556-563 (2001); by Iida K, Kurisu K, Arita K, Ohtani M., in an article entitled "Hyperemia prior to acute brain swelling during rewarming of patients who have been treated with moderate hypothermia for severe head injuries", published in J Neurosurg, vol. 98, pp. 793-799, (2003). However, these effects tend to reverse on rewarming. What is therefore required is a method that is safe for long duration use and could be sustained for the entire period of treatment and rehabilitation.

Prior art does not combine the benefits of CSF drainage with the added benefit of neuroprotection with hypothermia. CSF drainage is a first line treatment used to manage severely elevated intracranial pressure (>or =20 mm Hg) and improve outcomes in patients with acute head injury. However, CSF drainage alone provides a transient decrease in intracranial pressure without a measurable improvement in other indices of cerebral perfusion as disclosed by Kerr E M, Marion D, Sereika M S., in an article entitled "The effect of cerebrospinal fluid drainage on cerebral perfusion in traumatic brain injured adults", published in J Neurosurg Anesthesiol, vol. 12, pp. 324-333 (2000). Moreover, it has been demonstrated that hypothermia treatment significantly reduces excitatory amino acid and $NO_2$ concentrations, a finding which was associated with an improvement in cerebral perfusion pressure and oxygen saturation of the jugular venous blood ($SjO_2$) as disclosed by Yamaguchi S, Nakahara K, Miyagi T, et al., in an article entitled "Neurochemical monitoring in the management of severe head injured patients with hypothermia", published in Neurol Res, vol. 22, pp. 657-664, (2000). What is therefore required is a method that combines both CSF drainage and neuroprotection afforded by use of hypothermia.

Furthermore, prior art does not address stress related factors after injury to the brain. Because of the lack of specificity in mechanism of action, stress related factors are not down-regulated in a specific way using existing methods. What is required is a method that specifically modulates cortical-hypothalamic-pituitary-adrenal axis implicated in stress response, in a manner, that blunts the detrimental effects of stress related factors.

Similarly, prior art does not address the stimulation of pain pathways in traumatic brain injury. What is required is a method that would down-regulate nociceptive (pain) pathways but up-regulated anti-nociceptive pathways in the brain.

Prior use of hypothermia to prevent spinal cord injury has demonstrated clear benefits but there are methodological drawbacks limiting application of this approach in patients. In the spinal cord, regional spinal cord hypothermia increases spinal cord ischemia tolerance as disclosed by Meylaerts S A, De Haan P, Kalkman C J, et al., in an article entitled "The influence of regional spinal cord hypothermia on transcranial myogenic motor-evoked potential monitoring and the efficacy of spinal cord ischemia detection", published in J Thorac Cardiovasc Surg, vol. 118, pp. 1038-1045 (1999). Mild hypothermia attenuated the biphasic increase in CSF glutamate and corresponding development of neuronal damage after spinal cord ischemia in a study disclosed by Isikawa T, Marsala M., in an article entitled "Hypothermia prevents biphasic glutamate release and corresponding neuronal degeneration after transient spinal cord ischemia in the rat", published in Cell Mol Neurobiol, vol. 19, pp. 199-208 (1999). Others have described clinical benefits in patients after selective spinal hypothermia to prevent spinal cord ischemia as disclosed in articles by, Trowbridge C, Bruhn T, Arends B., in an article entitled "Selective deep spinal hypothermia with vacuum-assisted cerebral spinal fluid drainage for thoracoabdominal aortic surgery", published in J Extra Corpor Technol, vol. 35, pp. 152-155 (2003); and by Svensson L G, Khitin L, Nadolny E M, Kimmel W A., in an article entitled "Systemic temperature and paralysis after thoracoabdominal and descending aortic operations", published in Arch Surg, vol. 138, pp. 175-179 (2003). Clear benefits of epidural cooling was demonstrated by Cambria R P, Davison J K, Carter C, et al., in an article entitled "Epidural cooling for spinal cord protection during thoracoabdominal aneurysm repair: A five-year experience", published in J Vasc Surg, vol. 31, pp. 1093-1102, (2000). However, most authors use CSF drainage and avoidance of hypotension to minimize spinal cord ischemia. The use of the CSF drainage had been validated in a work disclosed by Coselli J S, Lemaire S A, Koksoy C, et al., in an article entitled "Cerebrospinal fluid drainage reduces paraplegia after thoracoabdominal aortic aneurysm repair: results of a randomized clinical trial", published in J Vasc Surg, vol. 35, pp. 631-639, (2002). It has been shown that subdural and epidural infusion cooling produced localized spinal cord hypothermia concurrently with uniformly distributed pressure increases and can result in spinal cord ischemia, as disclosed by Meylaerts S A, Kalkman C J, De Haan P, et al., in an article entitled "Epidural versus subdural spinal cord cooling: cerebrospinal fluid temperature and pressure changes", published in Ann Thorac Surg, vol. 70, pp. 222-227, (2000). What is therefore required is a method that combines hypothermia with CSF drainage and does not concurrently increase pressure in the subdural space.

Prior art has limited means to effect changes in cerebrospinal fluid and the acid-base balance in the brain. The fact that the closed system of CSF circulation is independent of atmospheric pressure allows venous volume and pressure to influence the overall pressure of the fluid. Methods implicating introduction of fluid into the CSF for the purpose of heat transfer would alter CSF volume, CSF pressure and could also alter acid-base balance of CSF as described in detail by Kazemi H, Johnson D C., in an article titled "Regulation of cerebral spinal fluid acid-base balance", published in J Physiol Rev, vol. 66, pp. 953-1037 (1986). It has been shown using continuous monitoring of cerebral acid-base balance and oxygen metabolism in the neurointensive care setting, that hypothermia rather than hyperventilation tends to improve cerebral acidosis and ischemia, as disclosed by Shiogai T, Nara I, Saruta K, et al., in an article entitled "Continuous monitoring of cerebrospinal fluid acid-base balance and oxygen metabolism in patients with severe head injury: pathophysiology and treatments for cerebral acidosis and ischemia", published in Acta Neurochir Suppl (Wien), vol. 75, pp. 49-55, (1999). Furthermore, it has been suggested that mild hypothermia could be beneficial in the prevention of severe encephalopathy in animal models of acute liver failure as a consequence of ammonia-induced impairment of brain energy metabolism as disclosed by Chatauret N, Rose C, Therrien G, Butterworth R F., in an article entitled "Mild hypothermia prevents cerebral edema and CSF lactate accumulation in acute liver failure", published in Metab Brain Dis, vol. 16, pp. 95-102 (2001). The choice of physiologic solution used for hypothermia could have a profound effect on viability of hippocampal tissue, which are particularly vulnerable to hypoxic-ischemia cellular injury as disclosed by Ikonomovic M, Kelly K M, Hentosz T M, et al., in an article entitled "Ultraprofound cerebral hypothermia and blood substitution with an acellular synthetic solution maintains neuronal viability in rat hippocampus", published in Cryo Letters, vol. 22, pp. 19-26, (2001). It is therefore desirable to have a device that could introduce specifically chosen constituents of physiological solution with the aim of altering acid-base balance to desirable levels, and at the same time positively altering cerebral perfusion.

Prior art may be difficult to implement in patients with subarachnoid hemorrhage (SAH). Animal models of severe SAH show significant mean apparent diffusion coefficient (ADC) changes calculated from diffusion-weighted magnetic resonance images, which are reversible by application of moderate hypothermia even when it is induced after a 60-minute delay. These findings support the concept of moderate hypothermia exerting a neuroprotective effect in severe SAH as disclosed by Piepgras A, Elste V, Frietsch T, Schmiedek P, et al., in an article entitled "Effect of moderate hypothermia on experimental severe subarachnoid hemorrhage, as evaluated by apparent diffusion coefficient changes", published in Neurosurgery, vol. 48, pp. 1128-1134 (2001). What is required is a flexible method that could easily be implemented alongside other surgical measures in the early post-SAH period.

Recent evidence suggest that mild hypothermia can alter cerebral vasoreactivity, and may enhance volatile anesthetic-induced vasodilatation of cerebral vessels as disclosed by Inoue S, Kawaguchi M, Kurehara K, et al., in an article entitled "Mild hypothermia can enhance pial arteriolar vasodilatation induced by isoflurane and sevoflurane in cats", Crit Care Med, vol. 30, pp. 1863-1869, (2002). What is required is a hypothermic device that could be integrated in the early and late surgical management of patients after SAH to prevent vasospasm without exposure to the risk of rebleeding in the early post-SAH period.

In the newborn, hypoxic-ischemic encephalopathy (HIE) remains one of the most important neurologic complications. Several experimental and clinical studies have shown that hypothermia is the most effective means known for protecting the brain against hypoxic-ischemic brain damage. Furthermore, recent data have suggested that platelet-activating factor (PAF) could play a pathophysiologically important role in the progression of hypoxic-ischemic brain injury as disclosed by Akisu M, Huseyinov A, Yalaz M, et al., in an article entitled "Selective head cooling with hypothermia suppresses the generation of platelet-activating factor in cerebrospinal fluid of newborn infants with perinatal asphyxia", published in Prostaglandins Leukot Essent Fatty Acids, vol. 69, pp. 45-50, (2003). What is required is a device adaptable for use in neonatology that could be selectively applied to the head to cool the cerebrospinal fluid in the ventricles through the anterior and posterior fontanelle.

SUMMARY OF THE INVENTION

The object of the present invention is to provide an improved patient temperature control system and method by applying cooling/rewarming to the CSF compartment, and is hereby referred to as 'cisternohypothermia'.

In particular, one object of the present invention is to provide rapid cooling/rewarming capabilities via heat exchange element, which can be used externally to apply cooling/rewarming to the CSF and blood in cerebral venous sinuses in the human brain, through the skin and bone, hence noninvasive 'indirect external cisternohypothermia'.

Another object of the present invention is to apply cooling/rewarming directly to the CSF in the ventricles by allowing heat transfer to occur by mixing of cooling/rewarming solution introduced through a ventricular catheter with CSF. This method is referred to as invasive 'direct internal cisternohypothermia'.

Another object of the present invention is to apply cooling/rewarming to the CSF in the ventricles by allowing heat transfer to occur between the CSF and cooling/rewarming solution flowing in a blind loop ventricular catheter. This method is referred to as invasive 'indirect internal cisternohypothermia'.

The present invention provides a method and apparatus for selectively cooling the brain to reduce the risk of brain injury from accidental medical conditions or planned medical procedures, and allows for selective cooling of the brain independent of core body temperature using noninvasive external conductive cooling of CSF pathway at cisterna magna and subarachnoid spaces and cerebral venous sinuses at the back of the head.

In neaonates, heat exchange with the CSF could be accomplished through the anterior and posterior fontanelle. The present invention provides a method and apparatus for selectively cooling the brain to reduce the risk of brain injury from accidental medical conditions or planned clinical procedures, and allows for selective cooling of the brain independent of core body temperature by invasive internal cooling of CSF in the cisterns of the brain.

The present invention includes steps of selectively controlling cerebral autoregulation by altering CBF and CPP; and cerebral vasoreactivity by altering ICP and MABP, accomplished by selectively altering CSF temperature and CMR, to further reduce the damage caused by brain injury in various accidental medical conditions or planned medical procedures.

The present invention could be specifically applied to maintain hypothermia and hence prevent hyperthermia in the brain during the rewarming phase of procedures requiring hypothermia of core temperature such as in cardiopulmonary bypass (CPB) surgery or liver transplant surgical procedure.

The present invention has an added advantage for selective cooling of the brain while minimizing the risk of frostbite, pneumonia or other thermal injury to the patient being cooled.

The invention is particularly advantageous in cardiac surgery, where it could be possible to employ normothermic CPB in patients undergoing coronary artery bypass grafting (CABG) or repair of intracardiac anomalies, with reduced risk exposure to ischemic neurologic sequalae.

The special embodiment of this invention is illustrated in the specifications, it includes block and schematic diagram for the format of the instrumentation, and how the system functions is shown by way of example. The human involved will be referred to as "patient" by way of example. These and other objects of the invention may become more apparent to those skilled in the art upon reviewing the description of the invention as set forth hereinafter, in view of its drawings.

DESCRIPTION OF THE PREFERRED EMBODIMENT

Figure 1:
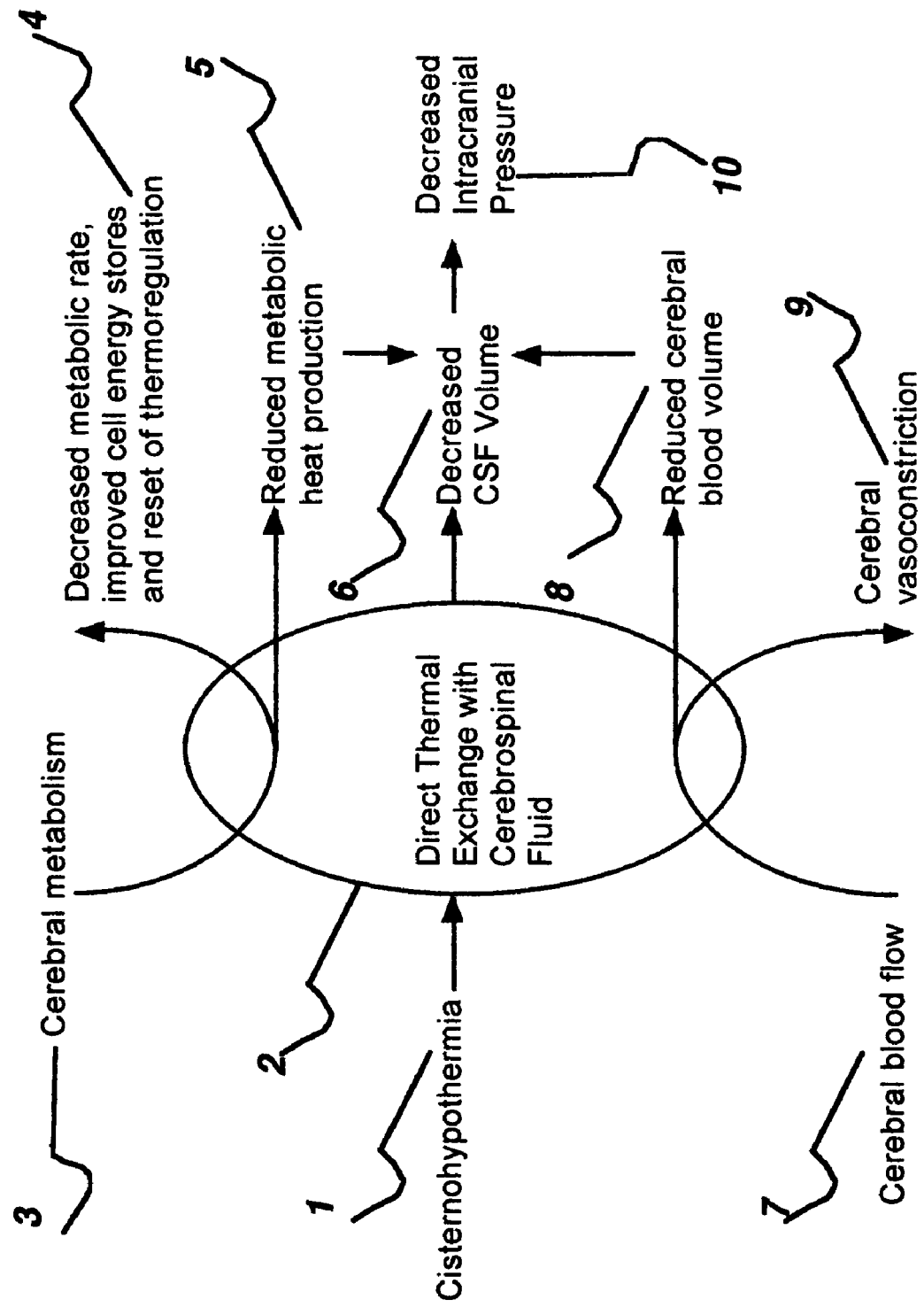
FIG. 1 shows the mechanism of transfer of heat to the CSF.

FIG. 1 shows the mechanism of transfer of heat to the CSF. As mentioned above, the method of application of cooling to lower the temperature of the CSF and is hereby referred to as 'cisternohypothermia'. Such a system 1 (cisternohypothermia) would have direct thermal exchange with the CSF compartment 2 cooling the CSF bathing the neural tissue and altering cerebral metabolism 3 by reducing cerebral metabolic rate 4 in neural cells, thereby conserving energy stores in cells. This will alter the balance between heat gain and heat loss following purely physicochemical considerations, however, this will also ultimately reset the thermoregulation by direct effects on neurons of central and peripheral afferents to the preoptic hypothalamus. There is a culminative effect of reduced metabolic heat production 5 and further cooling of the CSF and blood. The heat loss effect on the physical fluid characteristics of the CSF would cause a decreased CSF volume 6 and hence reduced intracranial pressure 10. During CSF pulsatile flow, heat exchange occurs with the cerebrovascular system and alters cerebral blood flow 7 resulting from the cooling effect and there would be reduction in cerebral blood volume 8 via reflex vasoconstriction 9. Analogous to 'cold pressor effect' the cerebral perfusion pressure would rise. There is an overall benefit of decreased CSF volume 6, decreased intracranial pressure 10, preserved vasoreactivity and autoregulation. The present invention would permit the use of hypothermia to desirably alter the major indices of cerebral autoregulation as disclosed by Rosner M. in an article entitled "Pathophysiology and management of increased intracranial pressure", in a book by Andrews B T. (ed.) entitled "Neurosurgical intensive care", published by McGraw Hill Inc., New York, pp. 57-112 (1993).

Figure 2:
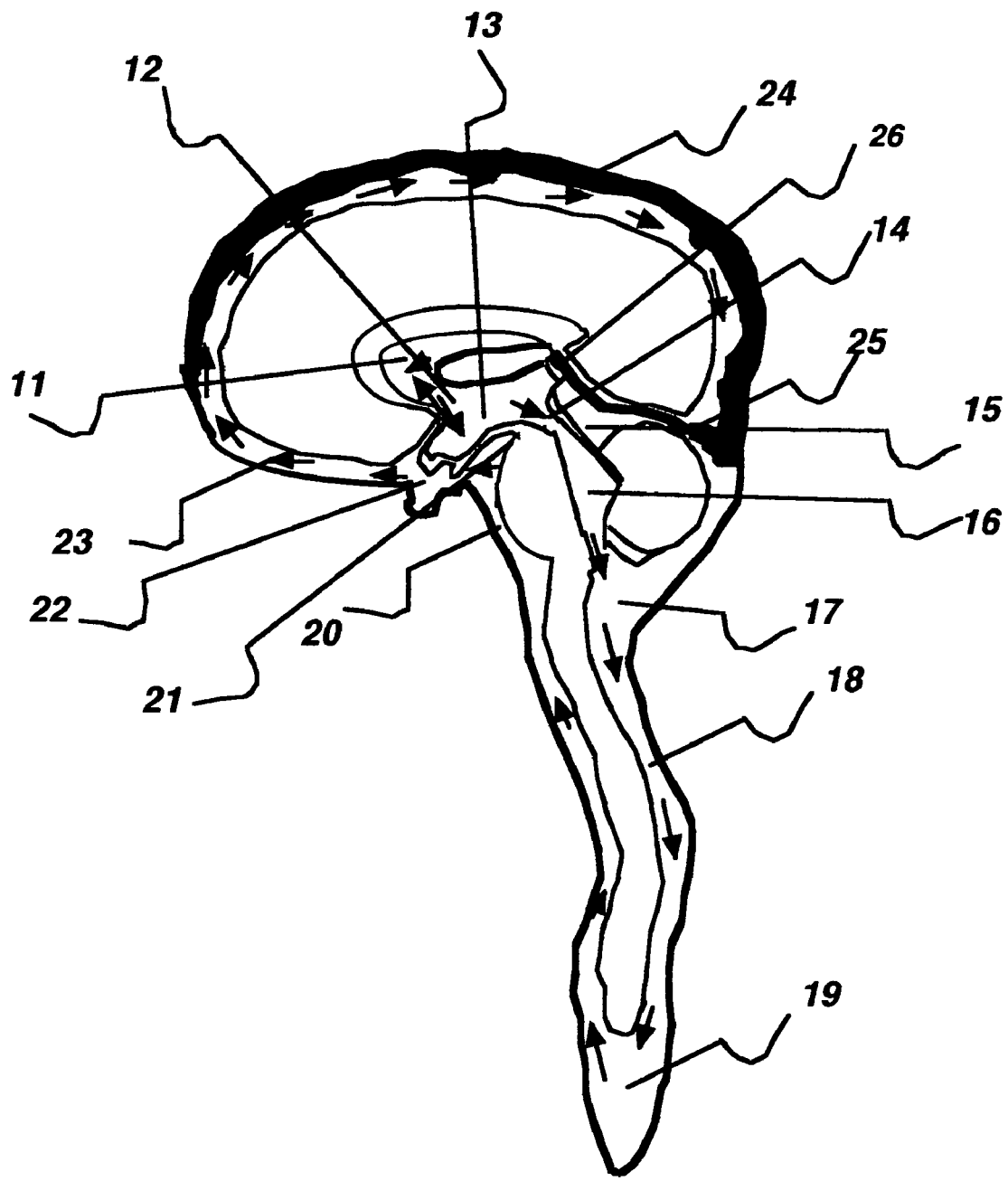
FIG. 2 shows the CSF pulsatile flow pathways as a means of heat exchange throughout the brain and spinal cord.

FIG. 2 shows the CSF pulsatile flow pathways as a means of heat exchange throughout the brain and spinal cord. The ventricles of the brain, the narrow spinal canal and the subarachnoid space are filled with CSF. CSF therefore baths both the inner and outer surfaces of the brain and spinal cord. It is a colorless liquid containing a few lymphocytes. Its composition differs from plasma in that it contains very little protein and has lower concentrations of K+, $Ca^{2+}$ and phosphate, but higher concentrations of Cl−. The glucose content is slightly lower and it is slightly more acidic (about 0.1 pH units) than plasma. Most of the components of CSF are secreted, some (for example Na+) by active transport mechanisms, from the vascular plexus (the chorioid plexuses) lining the lateral and third ventricles, CSF is formed at the rate of 0.3 ml/min or 500 mL/day in man, and its total volume is about 100-160 mL, making a renewal of the fluid every 4-5 hours. CSF pressure varies between 50-180 mm $H_2O$, depending on posture and the level of the neuraxis at which the pressure is measured. After a brain injury, there is alteration in CSF formation rate and a change in chemistry that could promote cellular injury. According to the teachings of the present invention, a means is provided to alter the chemistry of the CSF and promote neuronal viability. The cooling effect of CSF could spread to the entire brain through the pulsatile flow of CSF in the cisterns. The CSF flows from the lateral ventricles 11, through foramen of Monro 12, into the third ventricle 13, and via aqueduct of Sylvius 14 into the fourth ventricle 16. This region of the periaqueductal central gray area has been implicated in physical and emotional pain. The flow of cold CSF through the periaquaductal central gray area according to the teachings of the present invention reduces the stimulation of this subcortical region and could positively modulate responses to physical and psychological pain. Furthermore, CSF flow ensures that other vital brain stem areas are cooled. Between the roof of the fourth ventricle and the cerebellum lies the cisterna ambiens 15. The communication between the ventricular and subarachnoid fluids is by way of three foramina; a medial opening in the roof of the fourth ventricle, the foramen of Magendie, establishes a communication with the large cerebello-medullary cistern, and the cisterna magna 17. The lateral recesses of the fourth ventricle wind around the medulla, passing over the base of the inferior cerebellar peduncle; these recesses open to the subarachnoid 18 on the basal aspect of the brain as the foramina of Luschka. Each foramen is situated in the angle between the pons and medulla, and opens into the cisterna pontis 20 on the basal aspect of the brain stem. The CSF circulates to the lumbosacral region 19 in a bulk flow model. However, the rapid heat exchange could be explained by large pulsatile flow originating from the 'thalamic' or 'third ventricular' pump and as proposed by DuBoulay G, O'Connell J, Currie J, et al., disclosed in an article entitled "Further investigations on pulsatile movements in the cerebrospinal fluid pathway", published in Acta Radiologica, vol. 13, pp. 496-523 (1972). The CSF pulsatile movement that is dependent on the systolic and diastolic times of vascular pulsation has been documented using magnetic resonance imaging by Njemanze P C, Beck O J., disclosed in an article entitled "MR-Gated intracranial CSF dynamics: evaluation of CSF pulsatile flow", published in AJNR, vol. 10, pp. 77-80 (1989). The flow of CSF passes to other cisterns: cisterna interpeduncularis 21, cisterna chiasmatica 22, and cisterna frontalis 23. Heat exchange occurs with the cerebral venous sinuses: including the superior sagittal sinus 24, sinus rectus 25, and great vein of Galen 26.

Figure 3:
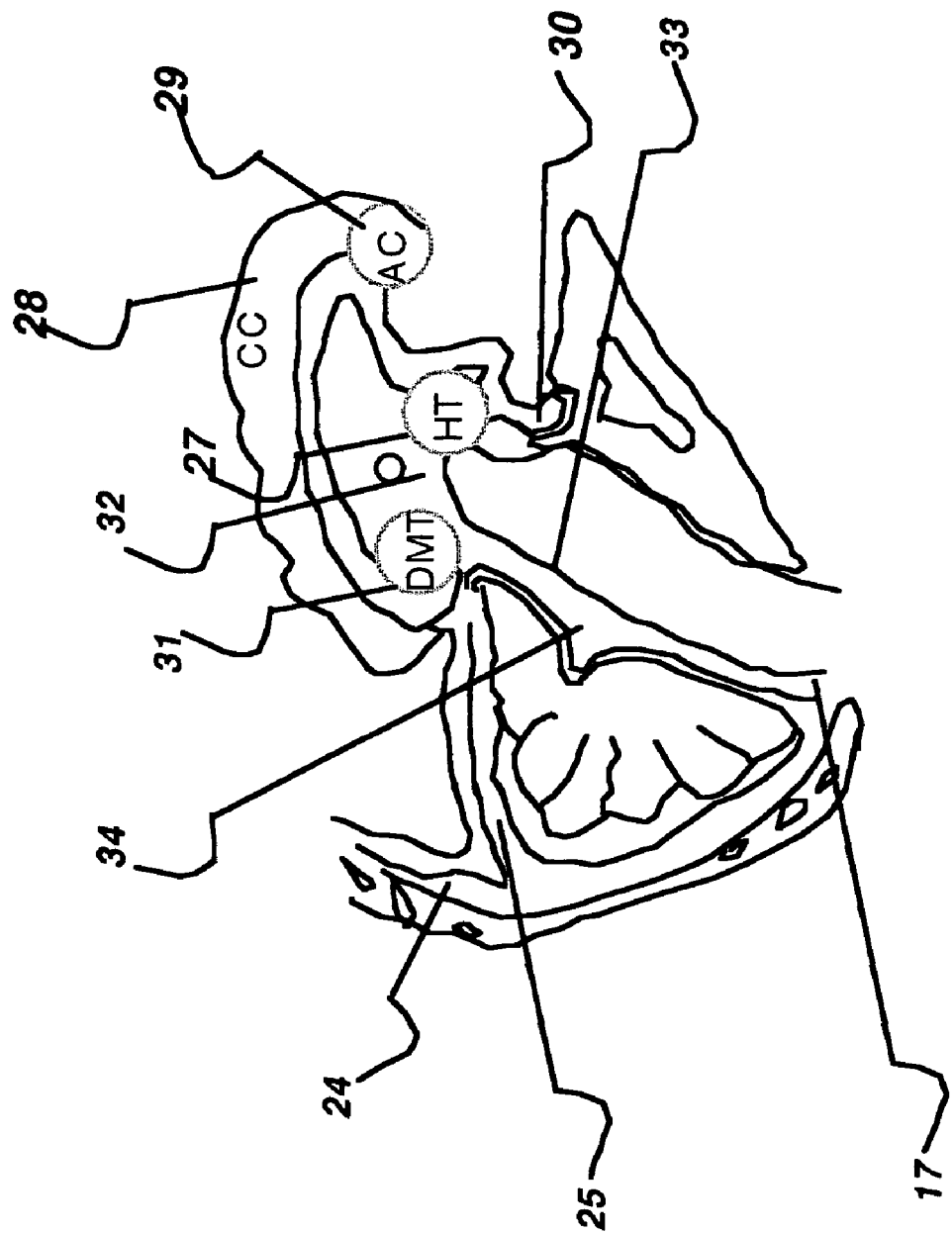
FIG. 3 shows the regulatory centers and their anatomic relationship to CSF pathways implicated in heat exchange.

FIG. 3 shows the regulatory centers and their anatomic relationship to CSF pathways implicated in heat exchange. In a neutral environment, the metabolic rate of humans consistently produces more heat than is necessary to maintain core body temperature at 37 degrees Celcius. The hypothalamus (HT) is the center of body temperature control. Neurons in both the preoptic anterior hypothalamus and posterior hypothalamus receive two kinds of signals—one from peripheral nerves that reflect receptors for warmth and cold and the other from the temperature of blood and CSF bathing the region. These two signals are integrated by the thermoregulatory center of the hypothalamus to maintain normal temperature as disclosed by Gelfand J A, Dinarello C A, Wolf S M., in an article titled "Fever, including fever of unknown origin", in a book by Isselbacher K. J., et al. (editors), entitled "Harrison's Principles of Internal Medicine", 13th Edition, published by McGraw-Hill Inc., New York: p. 82 (1994). These central afferent signals could be altered by the temperature of CSF bathing the region of hypothalamus 27 and that of blood flowing via cerebral sinuses (transverse sinus, straight sinus 25, sagittal sinus 24 and great vein of Galen 26), and furthermore via CSF pulsatile movement in the ventricles (lateral 11, third 13 and fourth 16), cisterna magnum 17 and basal cisterns 20-23. With the new, lower "thermostatic setting", signals go to various efferent nerves, particularly those sympathetic fibers innervating the peripheral blood vessels, which in turn initiate vasodilatation and promote heat loss. The hypothalamic thermoregulatory centers also sends signals to the cerebral cortex, particularly to centers that integrate the levels of emotional stress and cognition such as the central cingulate (CC) 28 and anterior cingulate (AC) 29; to the pituitary gland 30 to modulate the stress axis; as well as centers implicated in modulating the level of physical pair (anti-nociception) such as dorsomedial thalamus (DMT) 31 forming the walls of the third ventricle 32 and the periventricular central gray area including areas around the aqueduct of Sylvius 33 and fourth ventricle 34 as disclosed by Panksepp J., in an article titled "Feeling the pain of social loss," published in Science, vol. 302, pp. 237-239 (2003). Using temperature modulation and altering of activation patterns at these centers, it is thought that the level of post-traumatic stress syndrome and physical pain associated with traumatic head injury could be modulated using hypothermia according to the teachings of the present invention. There is mounting evidence that mild alterations in brain temperature can have a significant effect on functional outcome and histopathology following cerebrovascular accidents. In these studies, improvement in outcome was reported with mild hypothermia and worsened with mild hyperthermia. Modulation of ischemic brain injury by small alterations in brain temperature have been discussed. Temperature changes of either 1 or 2 degrees Celcius altered functional and histologic outcome in a canine model of complete cerebral ischemia, as disclosed by Wass C T, et al., in an article titled "Temperature changes of .gtoreq.1.degree. C. alter functional neurologic outcome and histopathology in a canine model of complete cerebral ischemia" published in Anesthesiology, vol. 83, pp. 325-335 (1995). Similarly, Warner D S, et al., disclosed in an article titled "Sevoflurane and halothane reduce focal ischemic brain damage in the rat: Possible influence in thermoregulation," published in Anesthesiology, vol. 79, pp. 985-992 (1996), discovered that a change in brain temperature of 1.2 degree Celcius altered functional and histologic outcome in a rat model of focal cerebral ischemia. Although the exact mechanism remains to be elucidated, there is evidence that such changes can have a significant effect on functional outcome and histopathology following cerebral ischemia.

Figure 4:
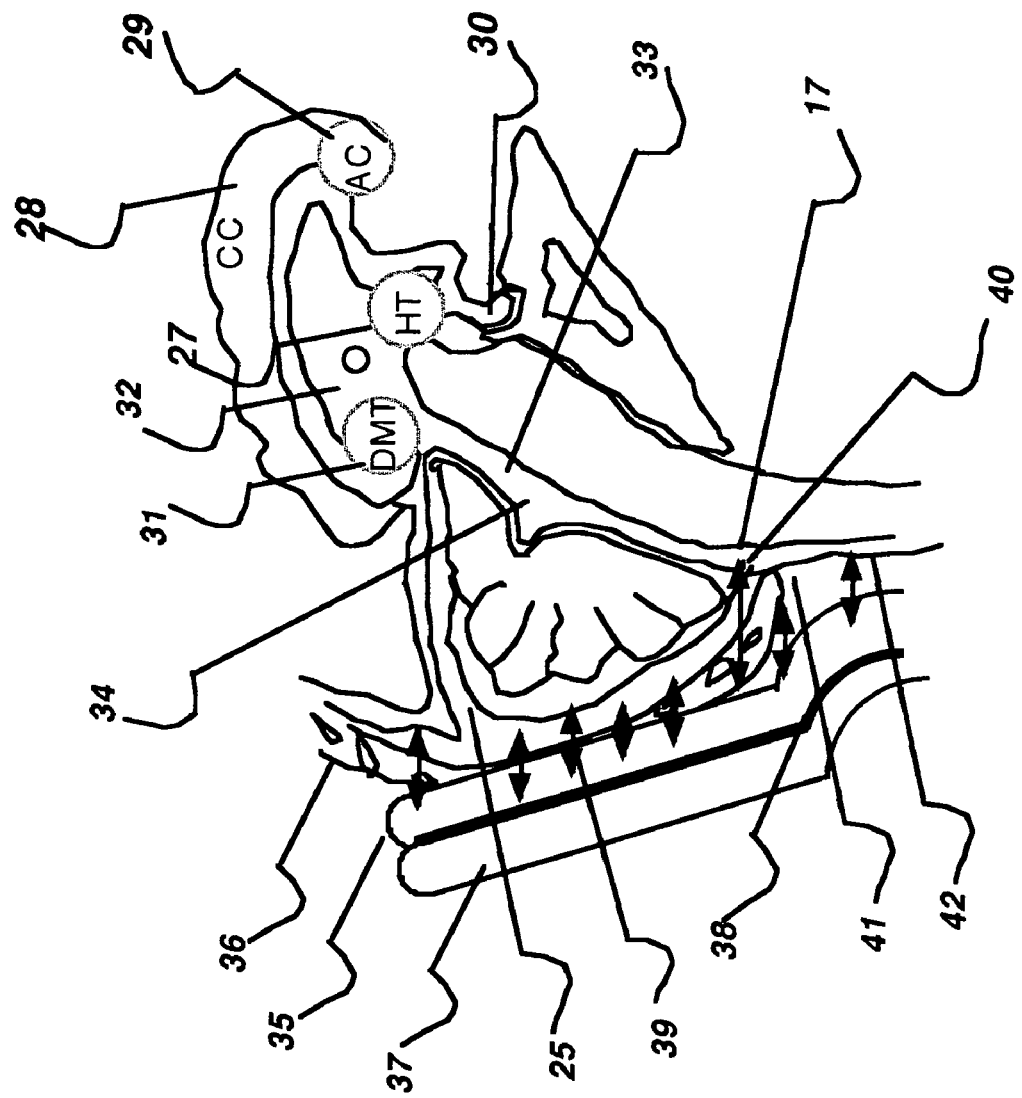
FIG. 4 shows the placement and heat exchange between the device for external cisternohypothermia and the CSF compartment in the brain.

FIG. 4 shows the placement and heat exchange between the device for external cisternohypothermia and the CSF compartment in the brain. The cooling element 35 which lies above the heating element 37 separated by a thin insulator 38 in the head and neck region and may extend to the lower spine region. The head rest is placed at the back of the head on the occipital bone 39 in close contact with the skin and thin bone covering the cerebral venous sinuses including the straight sinus 25 and transverse sinuses on the lateral sides, and the foramen magnum 41, cisterna magnum 17 and spinal subarachnoid space 42, through which heat exchange (double arrow head) is accomplished 40.

Figure 5A:
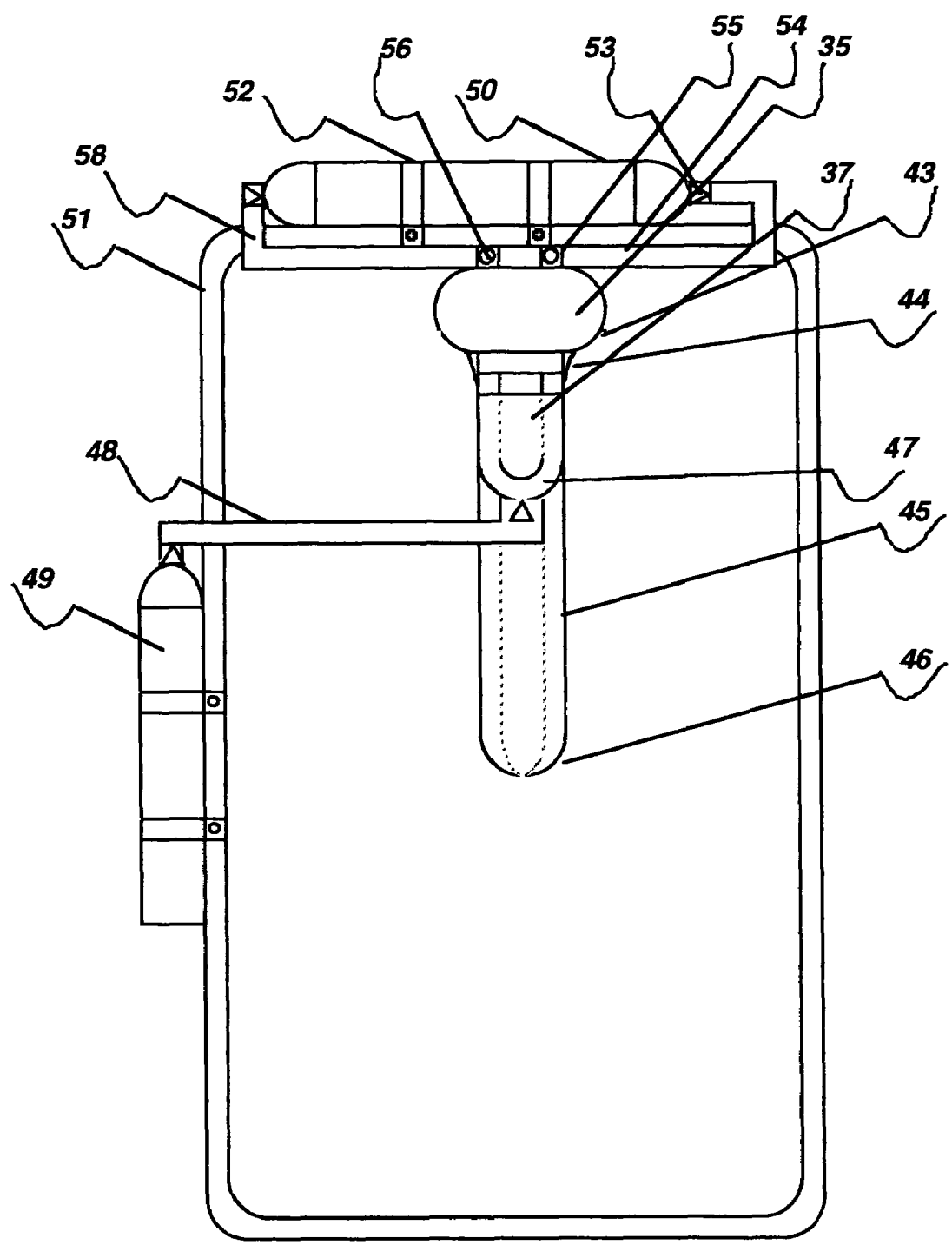
FIG. 5a shows one assembly of the device for external cisternohypothermia adapted for use in an ambulance.
Figure 5:
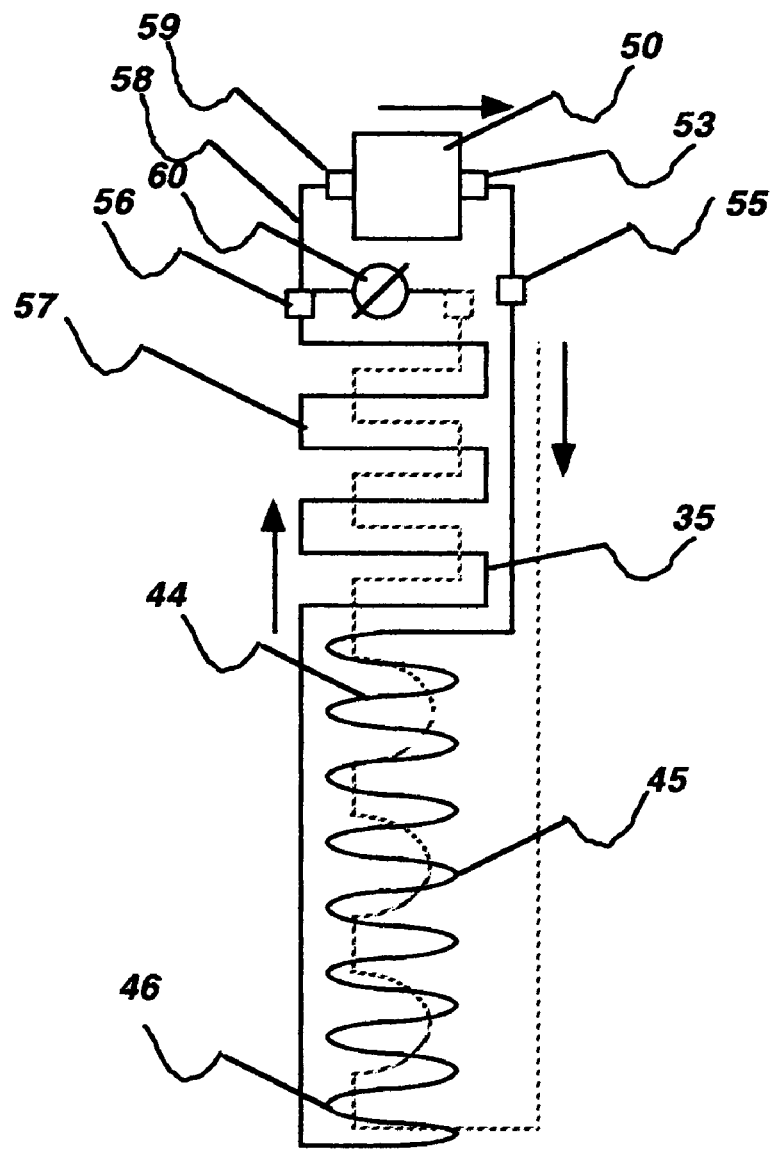
FIG. 5b shows the schematic diagram of the inside of the device for external cisternohypothermia.
FIG. 5c shows the cross-sectional layers of the device for external cisternohypothermia.
Figure 5:
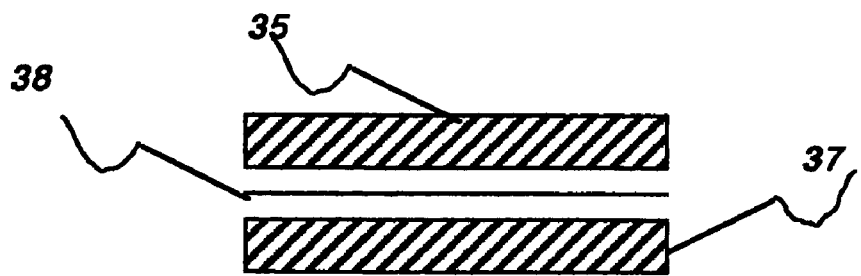

FIG. 5a shows one assembly of the device for external cisternohypothermia adapted for use in an ambulance. The cold 35 and heating 37 elements within the head rest 43 may extend to the cervical 44, thoracic 45, and lumbal 46 vertebrae respectively. In response to emergency, the patient is fitted with respiratory mask 47 administering oxygen through a breathing circuit from an oxygen tank 49. The device is affixed to a mobile stretcher 51 adapted for use to transport a patient in an ambulance. The device includes a source for cooling from a refrigerant pumped from a compressor/pump 50 clamped 52 to the frame of the stretcher 51. The gas is pumped through a valve 53 (see direction of arrows) into a system of pipes 54 attached to an inlet 55 to the cooling compartment 35.

FIG. 5b shows the schematic diagram of the inside of the device for external cisternohypothermia. The refrigerant is pumped 50 via a valve 53 into a pipe 54 and through the inlet valve 55 into a system of pipe coils in the cervical 44, thoracic 45 and lumbal extensions 46, where the gas evaporates and provides cooling of the CSF pathways in the cooling compartment 35 of the head rest 43 and flows out through a condenser 57 via an outlet valve 56 to returned to the pump 50 via a pipe line 58 and valve 59. The programmable flow rate and therefore cooling is regulated using a thermostatic control 60, which also controls the underlying rewarming element (dotted lines). Exemplary liquids comprising the coolant means include hydrofluorocarbons (HCFs), chlorofluorocarbons (CFCs), chlorodifluoromethane, polydimethylsiloxane, ethyl alcohol, liquid nitrogen, pentafluoroethane and distilled water. Exemplary gases comprising the coolant means include nitrous oxide and carbon dioxide. The device uses the battery power source of the ambulance by simply connecting it to the cigarette lighter socket of the vehicle, but in some cases, there is enclosed a small rechargable battery pack for power supply to the pump. In most cases, for transportation in the ambulance no rewarming is needed until arrival at the hospital, and the design for the purpose of emergency services within an urban area may exclude the rewarming circuit. However, in the aftermath of a major earthquake or other natural disasters, rewarming of patients using electrical blankets may be required. In place of electrical blanket for rewarming, some may prefer to use airflow thermal blanket for rewarming modified as described above. The use of thermal blankets has been described by prior art as disclosed in commonly-assigned U.S. Pat. No. 4,572,188 and U.S. Pat. No. 5,405,371. These two patents describe thermal blankets which include a plurality of communicating inflatable chambers.

FIG. 5c shows the cross-sectional layers of the device for external cisternohypothermia. The cooling 35 and heating 37 elements are separated by a thin insulator 38. Heating for rewarming phase is provided by use of an electrical blanket with the heating element arranged below the cooling element as shown.

Figure 6A:
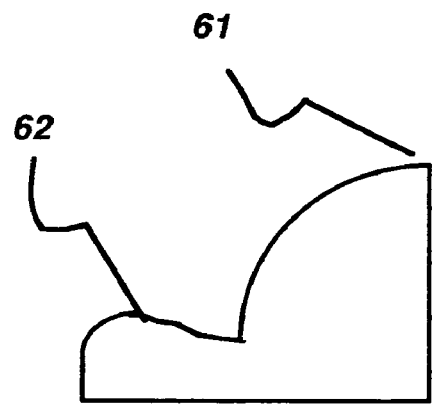
FIG. 6a shows the shape of another embodiment of the device adapted for first-aid use by first responders.

FIG. 6a shows the shape of another embodiment of the device adapted for first-aid use by first responders. The cooling element 35 for the portable head rest 61 is a fluid contained in vulcanized rubber material, by way of example. These portable easy to use and flexible to move packs are shaped as described in the drawings to cover the head and neck regions or including the entire thoracolumbal spine. They are adapted for short-term first-aid use at scenes of natural disasters, by way of example. Such packs could be made of special sealed-in fluid which neither hardens nor lumps, even in freezing temperatures. These non-refillable packs could be stored in freezers or refrigerators and replaced every few hours as desired. The design is aimed at maximizing contact with the head region overlying the cerebral venous sinuses, and CSF compartments in the third and fourth ventricle and the posterior horn of the lateral ventricles. In the neck region, contact with skin and bone overlying cisterna magnum is maximized by creating a hump 62 to fit the cervical lordosis.

Figure 6B:
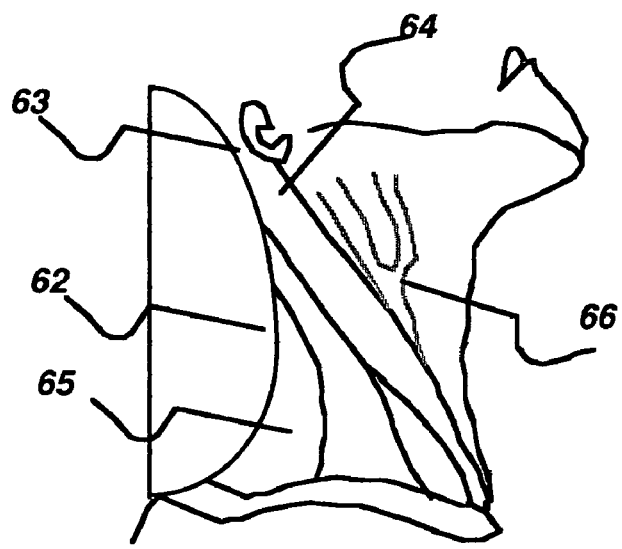
FIG. 6b shows the side view of anatomic landmarks used for placement and design considerations of the device.

FIG. 6b shows the side view of anatomic landmarks used for placement and design considerations of the device. The side edges of the device 63 are designed to run behind the edges of the stenocleidomastoid muscle 64 and parallel to the trapezoid muscle 65. This design restriction avoids both pressure and direct cooling of the carotid arteries 66 (particularly the carotid bifurcation) and prevents the elicitation of carotid baroreflex response that could cause hypotension. These design consideration applies to all present descriptions of the invention for external cisternohypothermia. Traditionally, packs in use for cooling this part of the body do not have this design consideration, quiet on the opposite, they are applied in the neck region over the carotid arteries and jugular veins with some pressure, contrary to the teachings of the present invention. Prior art demonstrating application of cooling to the neck region above the carotid arteries in order to cool the flowing blood, are disclosed in U.S. Pat. No. 6,547,811 to Becker et al. and U.S. Pat. No. 5,916,242 to Schwatz. Materials that could be used for the present invention, could be made from materials similar to that from which Dura-Cold Packs are made, obtainable from Baxter Healthcare Corporation, McGaw Park, Ill. Rewarming is accomplished simply by removing the pack. The cooling element could be made from ice-slurries. For background information on phase-change slurries, and specifically ice slurries, see Kasza K E, Chen M M. Assessment of impact of advanced energy transmission fluids on district heating and cooling systems (phase I), Argonne National Laboratory, 1987.

Figure 6C:
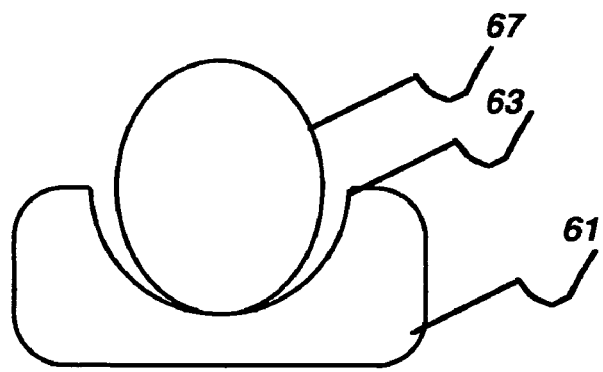
FIG. 6c shows the top-side view of placement of the head within the head rest of the device adapted for first-aid use by first responders.

FIG. 6c shows the top-side view of placement of the head within the head rest of the device adapted for first-aid use by first responders. The head 67 when placed within the head rest 61 creates a concave depression.

Figure 6D:
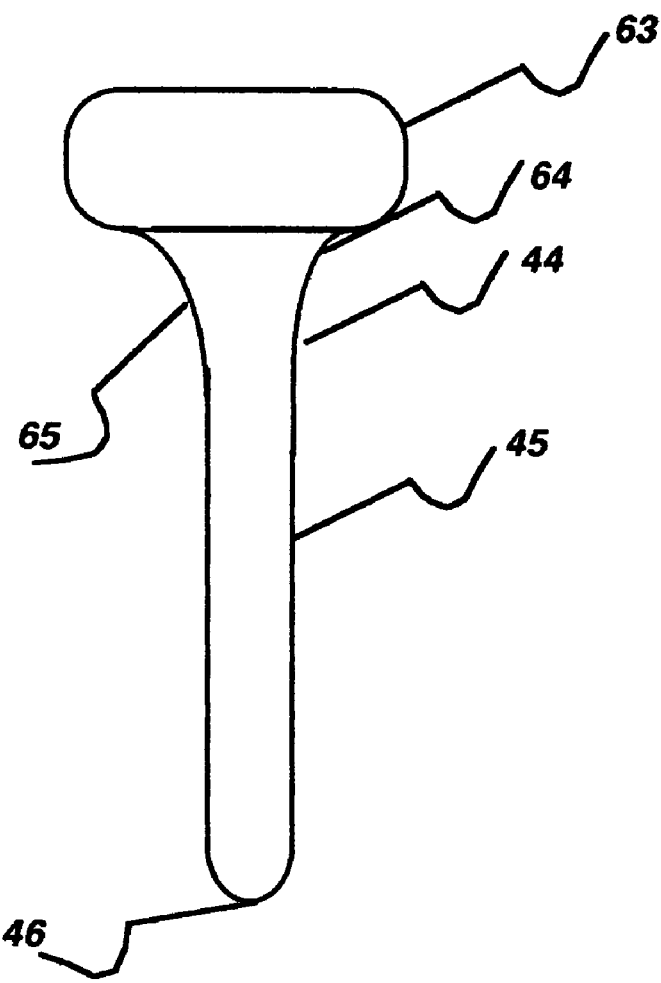
FIG. 6d shows the top view of the device adapted for first-aid use by first responders.

FIG. 6d shows the top view of the device adapted for first-aid use by first responders. The head rest 61 is shaped to be continuous with other parts, both edges are positioned behind the ears 63 enveloping the area of the cerebral transverse venous sinus from both sides. As well as covering the neck region from the stenocleidomastoid muscle edge 64, along the trapezoid muscles 65 to the spinal extension, between the scapulae, avoiding placement over the lung regions. The cervical 44, thoracic 45 and lumbal 46 extensions are continuous with the cervical and head rest 61 compartments allowing free flow of fluid to all parts of the device.

Figure 6E:
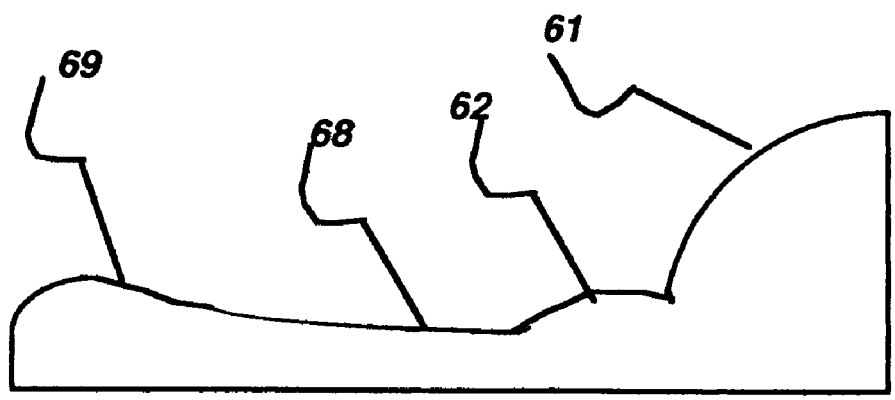
FIG. 6e shows the side view of the device adapted for first-aid use by first responders.

FIG. 6e shows the side view of the device adapted for first-aid use by first responders. The cervical lordosis is fitted with a cervical convex hump 62, conversely, the thoracic kiphosis is fitted with a thoracic concave depression 68, and similarly the lumbal lordosis is fitted with lumbal convex hump 69. Such detail of design will allow maximum contact with the areas to be cooled. Furthermore, size selection would facilitate that each patient is correctly matched to the appropriate device. Other more generic designs are possible, including flexible surface designs that assumes body surface contour on contact for infant, children and adult sizes.

Figure 7:
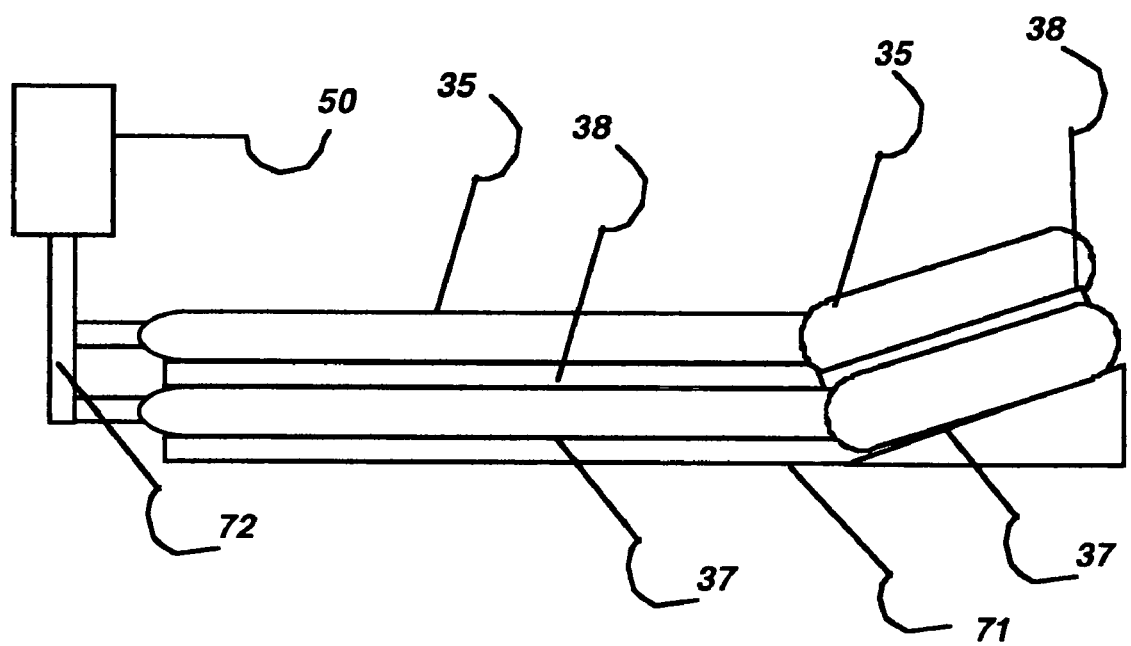
FIG. 7 shows the embodiment of the stationary device with cooling and warming fluid source.

FIG. 7 shows the embodiment of the stationary device with cooling and warming fluid source. Exemplary liquids comprising the coolant include HCFs, CFCs, chlorodifluoromethane, polydimethylsiloxane, ethyl alcohol, liquid nitrogen, pentafluoroethane and distilled water. Exemplary gases comprising the coolant means include nitrous oxide and carbon dioxide. The cooling and rewarming using distilled water could be accomplished from a source equipped with a compressor 50 and heater, for example the RK-2000 hypo/hyperthermia unit (Baxter Healthcare Corporation, McGaw Park, Ill.). In yet another modification, the device could be used in conjunction with Rheostat flow control and Integrated Pump System from Orthopedic Medical Supplied, Corona, Calif. The device is placed on a bed 71 and the cold/warm distilled water is supplied via plastic hose 72 to the cold 35 and warm 37 elements separated by a thin insulator, both compartments are filled in turn during the cooling or rewarming phase respectively. The rationale for dual chambers for cold and warmth arises when two different chemical substances, for example carbon dioxide and distilled water are used for cold and warmth respectively. However, when one substance for example cold and warm distilled water is used, only one chamber is required.

Figure 8:
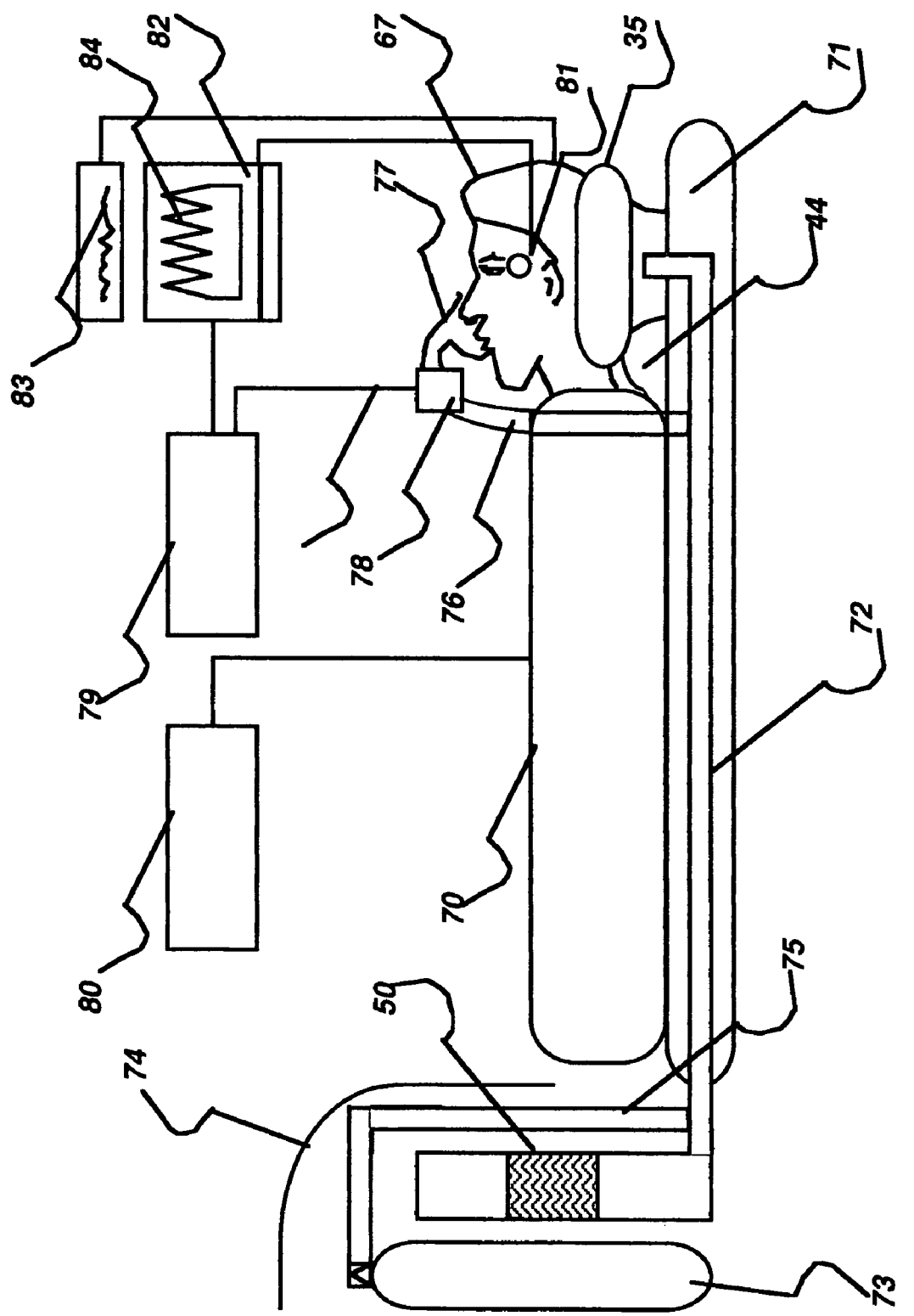
FIG. 8 shows the embodiment of the stationary device used in conjunction with other monitoring devices in a neurointensive care unit.

FIG. 8 shows the embodiment of the stationary device used in conjunction with other monitoring devices in a neurointensive care unit. The patient 70 is placed on a bed 71, on which the device is affixed. When preferred a velcro surface at the base of the device could be used to position the device in the center of the bed, before placement of the patient 70. The head 67 is placed on the cold compartment 35. In one modification the same compartment could be used for cooling and rewarming phases, one after the other. The neck region lies in contact with the cervical spine extension 44 of the device. The thoracic and lumbal extensions (not visible) are placed in the center of the back along the spine. The source pipe 72 provides the cooling/rewarming from a pump 50 drawing fluid from a fluid reservoir, for example, the RK-2000 hypo/hyperthermia unit (Baxter Healthcare Corporation, McGaw Park, Ill.). The patient is ventilated from an oxygen tank 73 placed behind the wall 74 of the intensive care, with gas supplied through an air hose 75 to a breathing circuit 76 and then to the mask 77. The partial pressure of carbon monoxide ($PCO_2$) within the exhaled air is measured by a sensor 78 connected to a capnometer 79. The blood pressure 80 is monitored invasively using blood pressure recordings obtained with a radial artery fluid coupled system (for example, pvb, Kirchseeon, Germany) or noninvasively with an automatic sphygmomanometer (for example, Dinamap, Critikon, Fla.). Cerebral blood flow velocity could be obtained using a 2 MHz transcranial Doppler (TCD) probe placed on the temporal bone 81, and connected to a TCD instrument (for example, Multi-Dop T, DWL, Sipplingen, Germany) 82. The intracranial pressure could be monitored using an intraparenchymal sensor 83 (Camino V420, San Diego, Calif., USA or Spielgelberg, Brain Pressure Monitor, Spiegelberg KG, Hamburg, Germany) or through an external ventricular drain. A temperature probe could be inserted to obtain the temperature of the circulating CSF, especially when the patient has indication for placement of a ventricular catheter. The intracranial pressure waveform 83, and transcranial Doppler waveform 84, blood pressure and PCO2 along with other variables could be displayed and integrated with the hypothermic cooling temperature values, by the microprocessor into a servo-controlled monitoring and regulatory system with thresholds established by the surgeon and anesthesiologist.

Figure 9A:
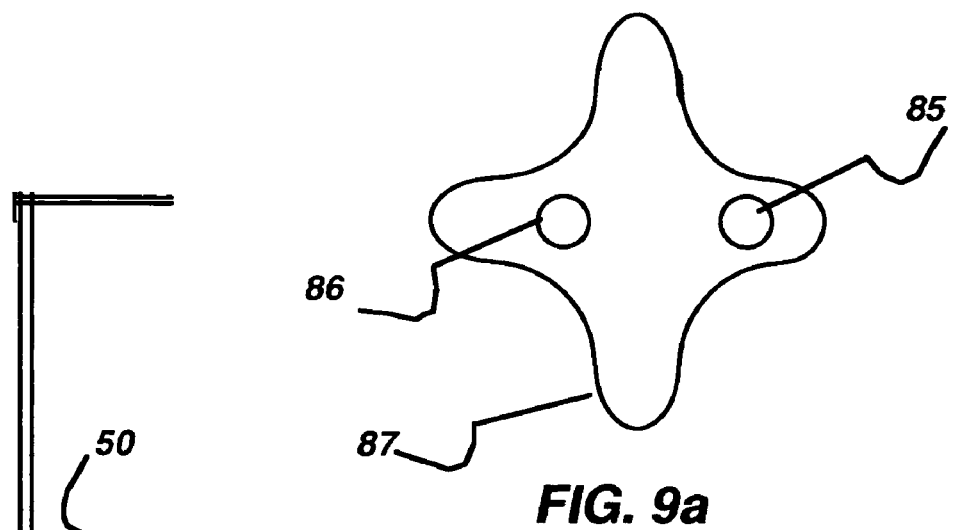
FIG. 9a shows another embodiment of the present invention adapted for application of external cisternohypothermia in neonates.

FIG. 9a shows another embodiment of the present invention adapted for application of external cisternohypothermia in neonates. The device has an anterior end with a placement site for the anterior fontanelle 85 and a posterior end with a placement site for the posterior fontanelle 86. The lateral flaps 87 cover the parieto-temporal areas lying above the posterior horns of the lateral ventricles. The device is suitable for use in neonates with perinatal asphyxia, normal pressure hydrocephalus and ventricular cysts.

Figure 9B:
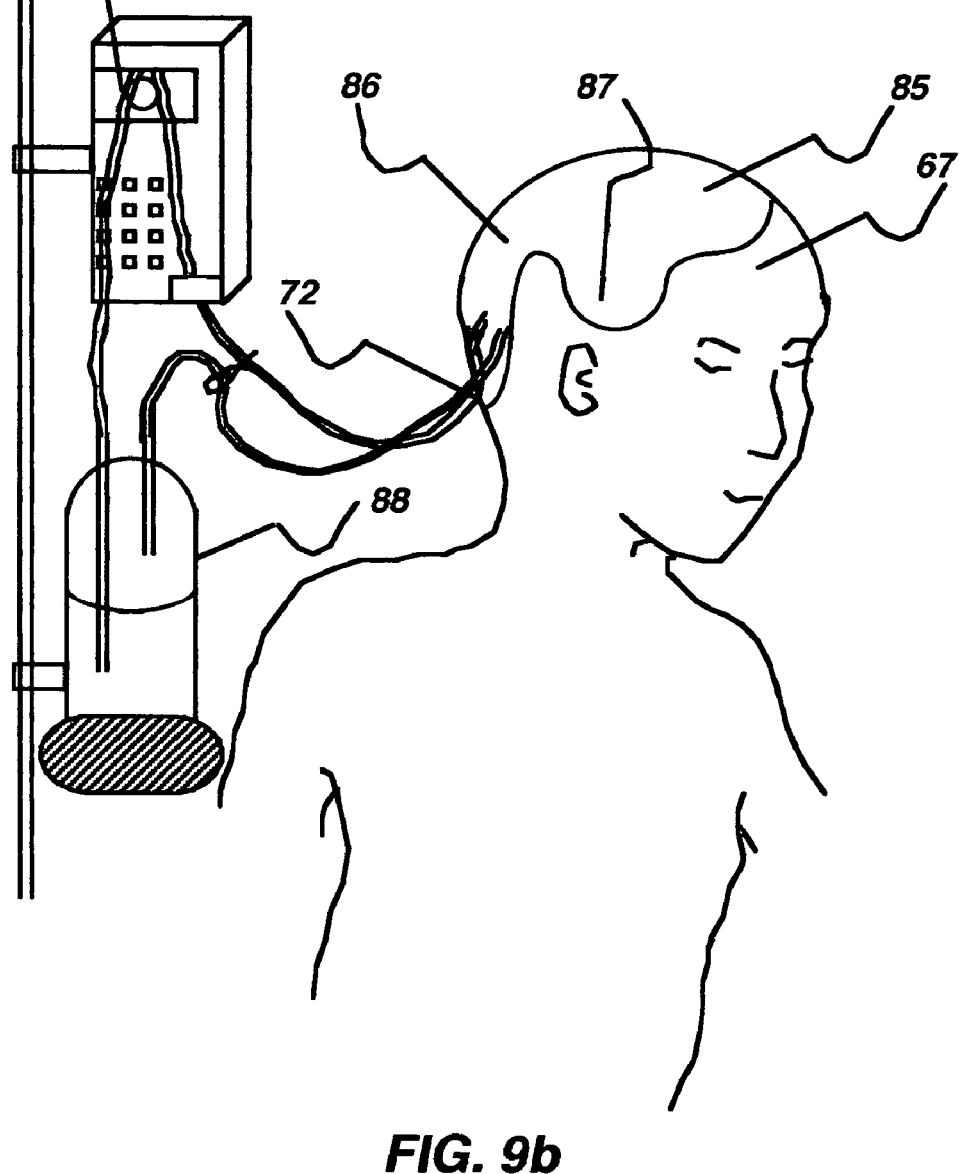
FIG. 9b shows one application of the device for external cisternohypothermia on the neonatal brain.

FIG. 9b shows one application of the device for external cisternohypothermia on the neonatal brain. The device is placed on the head 67 such that the anterior fontanelle 85 and posterior fontanelle 86 are covered with the lateral flaps 87 lying above the temples. The device compartment has a pipe system 72 from a reservoir 88. The design facilitates rapid cooling and rewarming of the CSF compartment by use of a pump system 50 circulating cooled or rewarming fluid through the pipe 72 from and to a reservoir 88. Alternative sources of cold and warm fluid could be used, for example, the RK-2000 hypo/hyperthermia unit (Baxter Healthcare Corporation, McGaw Park, Ill.).

Figure 10:
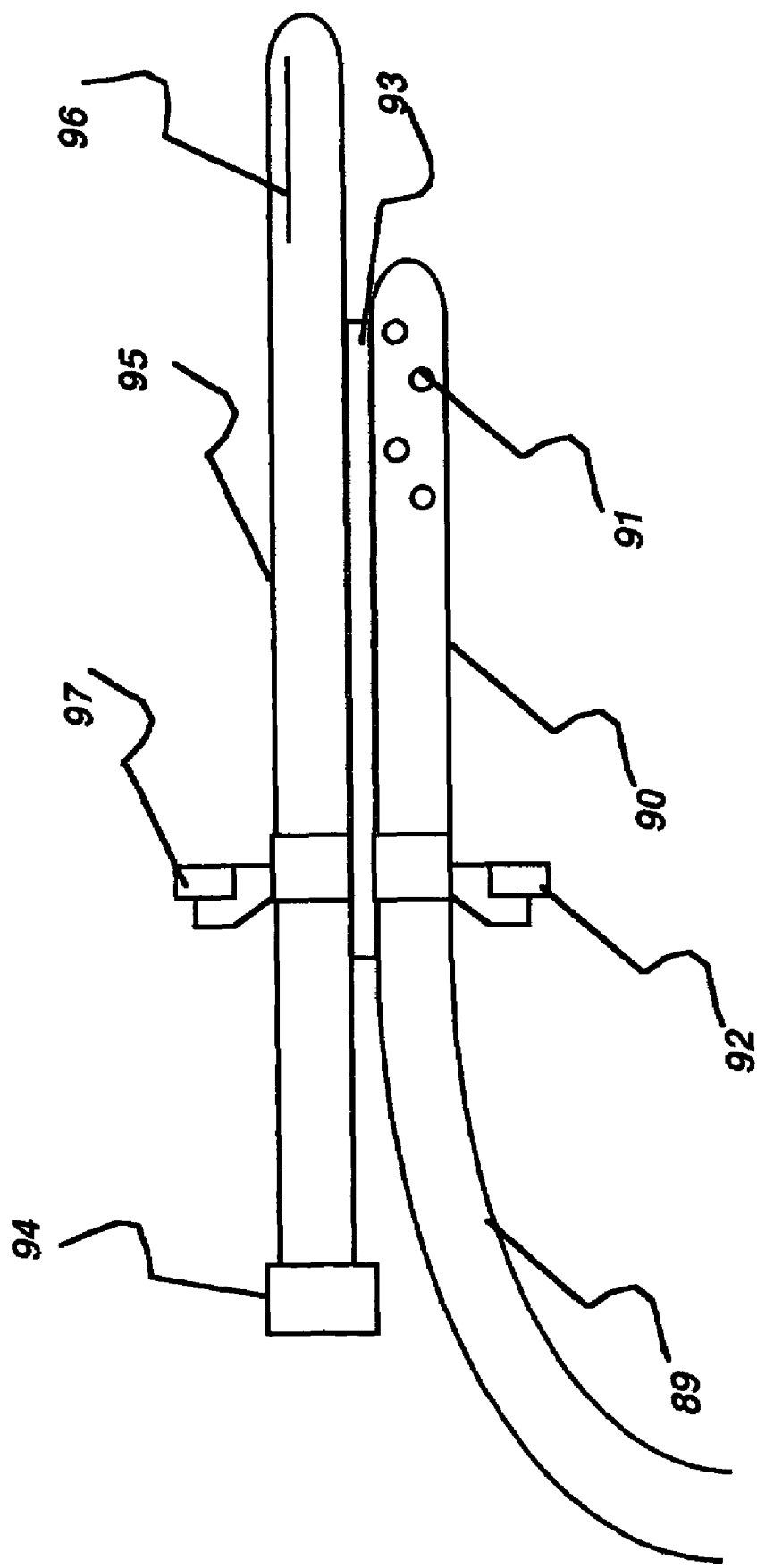
FIG. 10 shows another embodiment of the present invention adapted for placement in the intracranial ventricles for drainage and internal cisternohypothermia.

FIG. 10 shows another embodiment of the present invention adapted for placement in the intracranial ventricles for drainage and internal cisternohypothermia. There are two catheters that could be physically joined together on a firm polypropylene base, and implanted into the ventricle through a burr hole or twist drill. A design in which both catheters are joined to form a double lumen catheter, in which one lumen is for drainage and the other for heat exchange, is hereby referred to as 'double barrel' ventricular catheter. The two catheters, one is similar to a conventional intracranial ventricular catheter usually made of silicone elastomer tubing impregnated with white barium sulfate to provide radiopacity, with a proximal end 89, a mid portion 90 and a distal end with perforated holes 91. As is conventionally accepted, black length markers made of a graphite-impregnated silicone elastomer are positioned on the catheter at points 5, 10, 15 cm from the proximal tip to enable the surgeon to gauge the depth of the penetration of the catheter into the lateral ventricle. There is a right angle clip 92 designed to angulate the catheter so it may lie within the mid portion of the lateral ventricle. The catheter is joined to the cooling catheter by a relatively firm polypropylene plate 93 incorporated in the catheter design to provide some rigidity and resistance to catheter kinking, and is a heat insulator. The second heat-exchange catheter provides cooling of the CSF by introducing cold physiologic solution of known constituents into the CSF compartment at a predetermined rate. The heat-exchange catheter has a proximal end 94 that connects to the source of cold fluid, a mid portion 95 and a distal portion with four slit openings 96 at 90 degrees in the catheter wall near the distal tip. These slit openings are designed to provide protection from retrograde flow and occlusion of the catheter. There is a right angle clip 97 that is designed to angulate the catheter so that the proximal portion 94 is turned away from the proximal end of the other ventricular drainage catheter 89.

Figure 11:
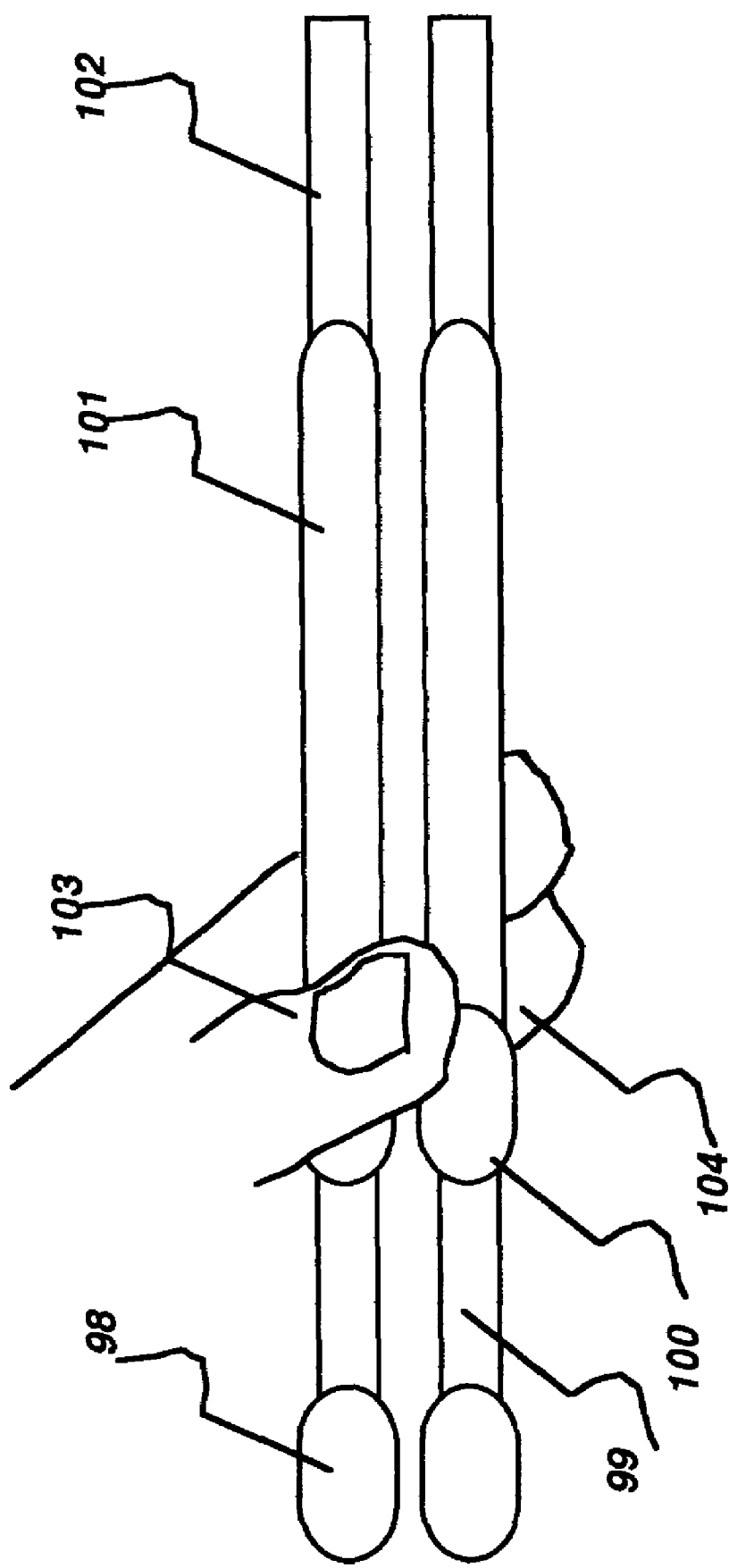
FIG. 11 shows the use of the 'double barrel' catheter introducer held in preparation for insertion of the double barrel catheter into the ventricle.

FIG. 11 shows the use of the 'double barrel' catheter introducer held in preparation for insertion of the double barrel catheter into the ventricle. This disposable quick release ventricular introducer has a stylet grip 98 for holding, a silicon tube "spring" 99, a shaft grip 100, a stainless steel shaft 101 which covers the main stainless steel stylet 102. The blunted tip of the stainless steel stylet is used for insertion into the slit hole 96 of the catheter in preparation for introduction into the ventricle. The ventricular introducer is usually held between the thumb 103 and index finger 104. For use with the double barrel catheter, a pair of catheter introducers are held between the first and third fingers of one hand like a pair of Chinese chopsticks. Their tips are inserted into the perforated holes of both catheters, and both catheters and their introducers are held firmly together. A suitable ventricular catheter introducer could be obtained from Pudenz-Schulte Medical, Santa Barbara, Calif.

Figure 12:
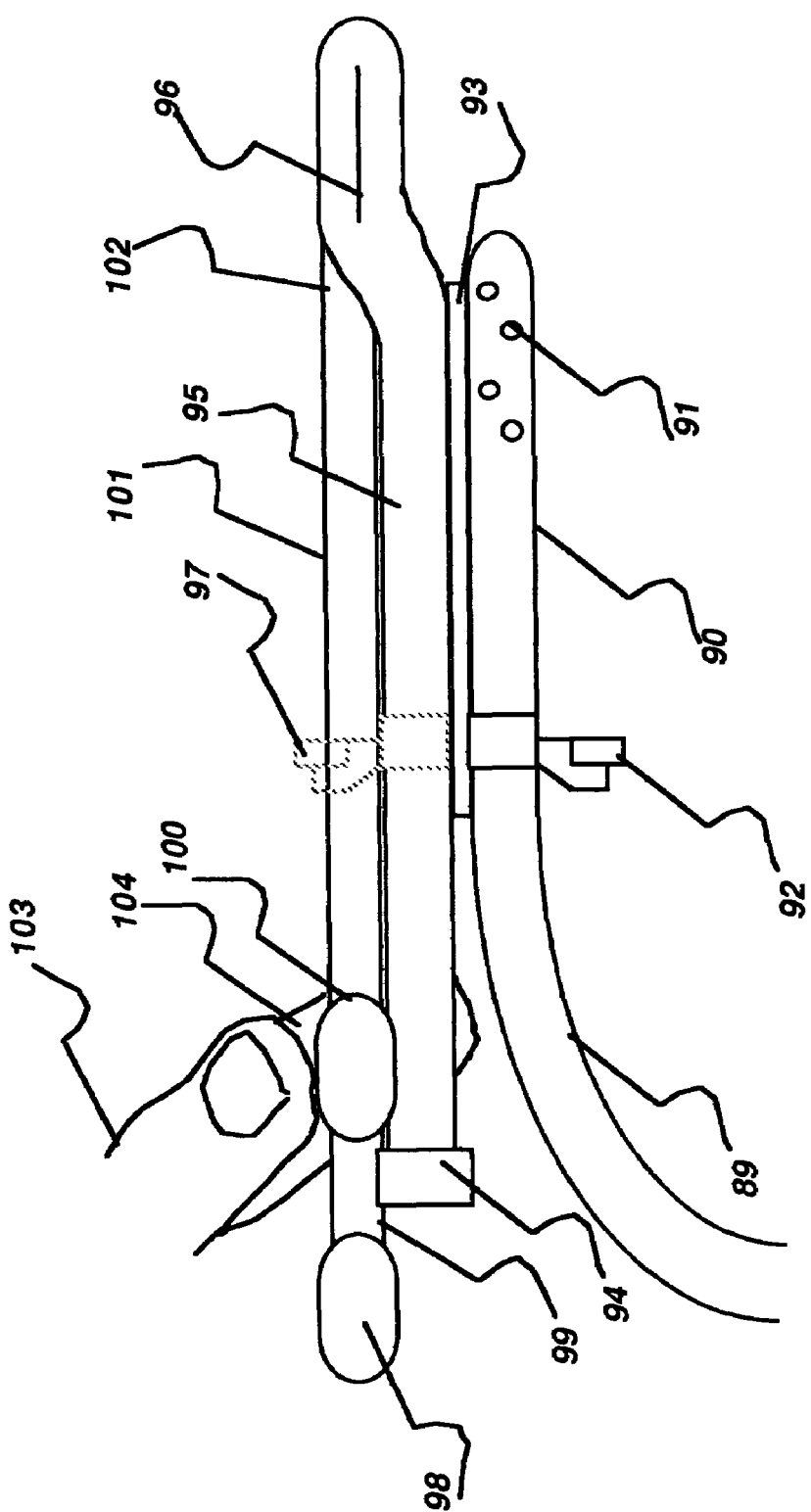
FIG. 12 shows the sequential introduction of the catheter introducer into the heat-exchange catheter of the 'double barrel' catheter before placement into the ventricle.

FIG. 12 shows the sequential introduction of the catheter introducer into the heat-exchange catheter of the 'double barrel' catheter before placement into the ventricle. The introducer tip is inserted into the heat-exchange catheter slit opening 96. This is followed subsequently by introduction into the perforated hole 91 of the drainage catheter in a similar manner. Both catheter introducers along with the double barrel catheters are introduced into the ventricle.

Figure 13:
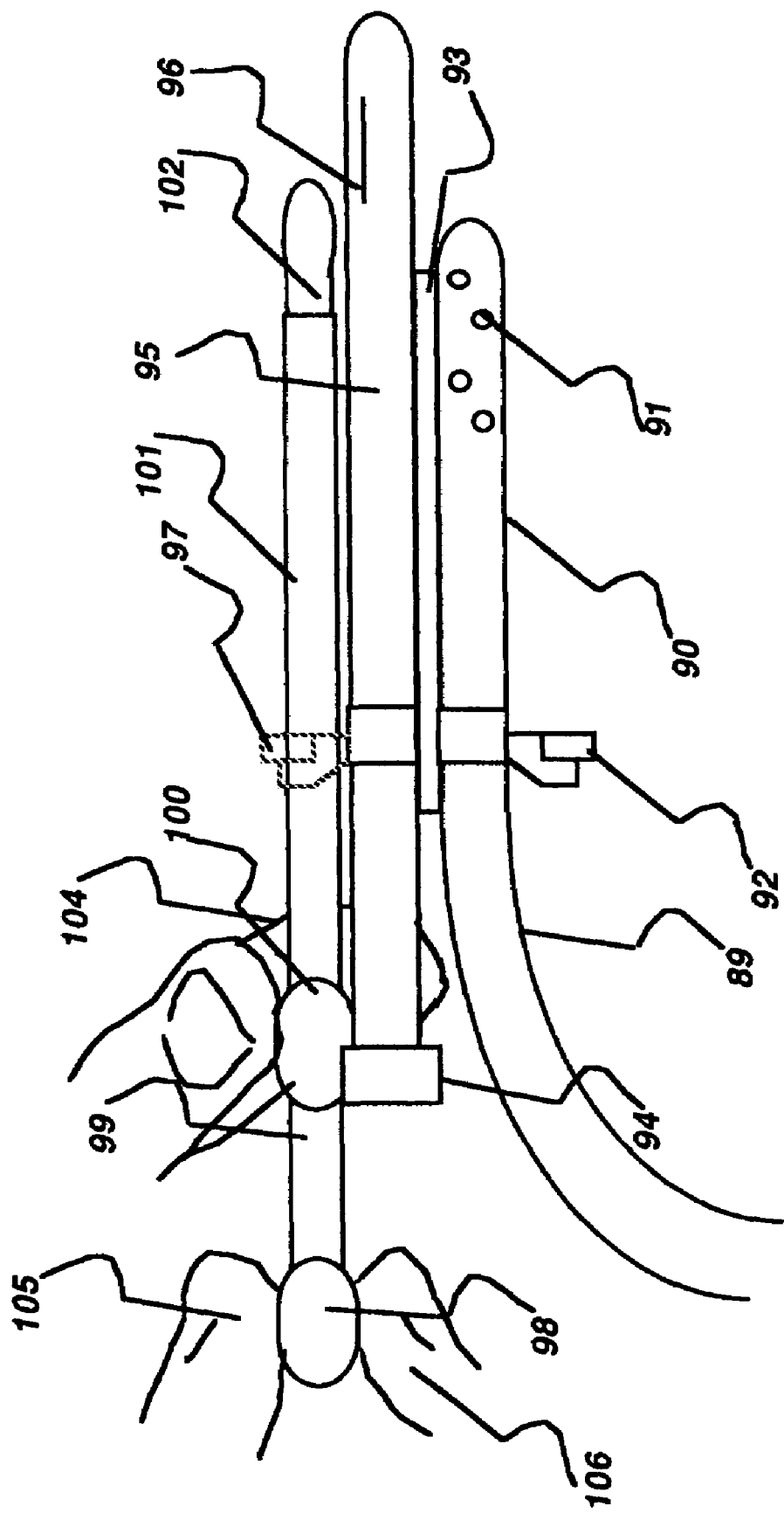
FIG. 13 shows the sequential release of the 'double barrel' catheter from the introducer into the ventricle.

FIG. 13 shows the sequential release of the 'double barrel' catheter from the introducer into the ventricle. The introducer is held firmly at the stylet grip 98 between the thumb and index finger 104 of one hand and withdrawn with the first 105 and index finger 106 of the other hand. A swift action that pulls back the stylet grip 98 by about 1.5 cm assures release of the catheter into the ventricle. The introducer is now withdrawn from the ventricle.

Figure 14:
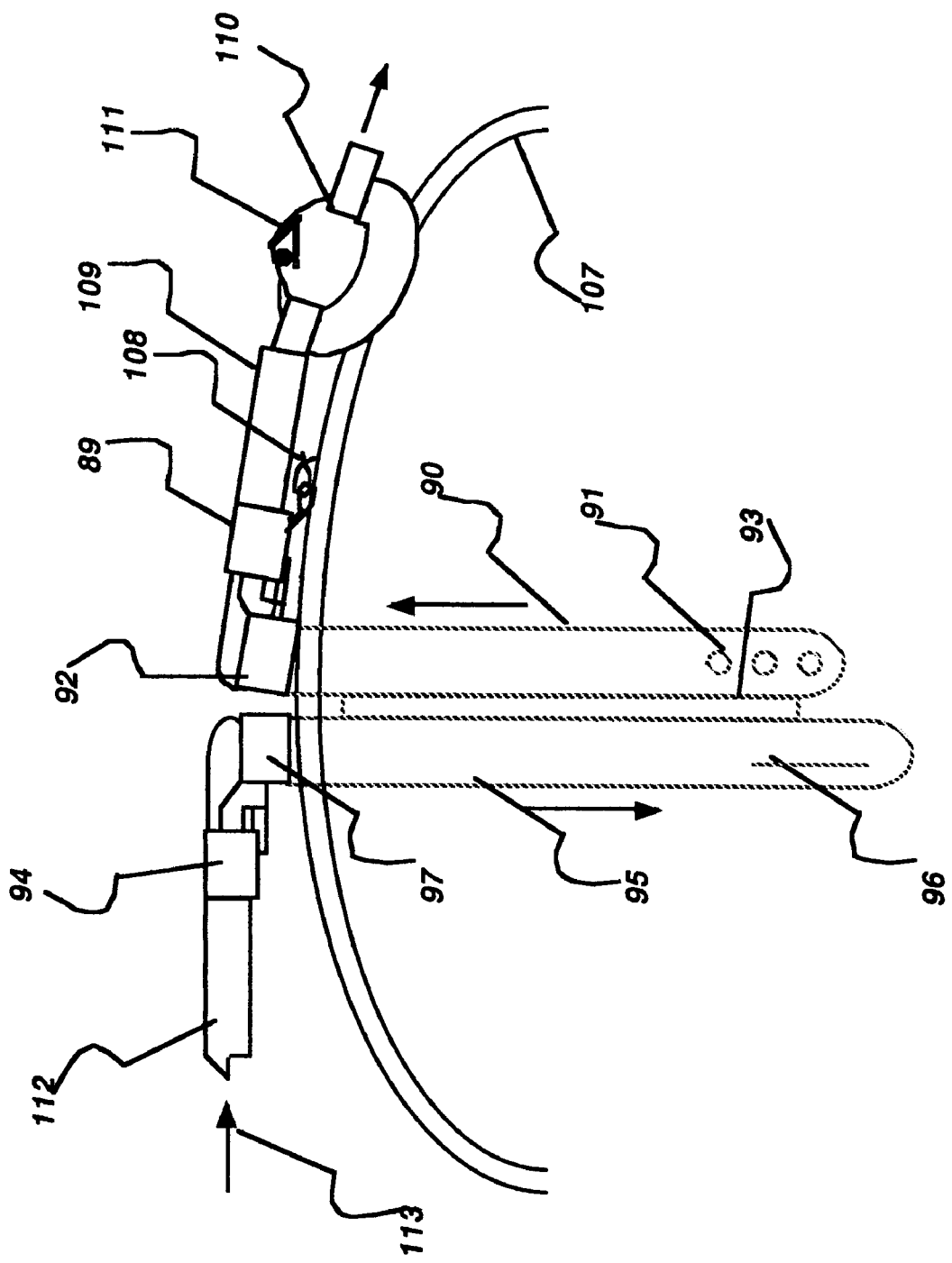
FIG. 14 shows the preferred embodiment of the setup of the double barrel catheter within the ventricle.

FIG. 14 shows the preferred embodiment of the setup of the double barrel catheter within the ventricle. The right angle clips 92 and 97 are used to bend both catheters to 90 degrees in opposite directions at the point where they exit the twist drill or burr hole. The use of the clips for this purpose is optional. The right angle clip 92 is secured to the adjacent tissue by passing sutures through the two suture flanges on the sides of the clip 108. The extracranial portion 109 of the ventricular catheter is connected to the CSF-flow control valve 110, with markings showing low pressure (one dot) and direction of flow (arrow head) 111, by way of example. The supply line 112 with cooling fluid 113 is connected to the heat-exchange catheter at the proximal end 94.

Figure 15:
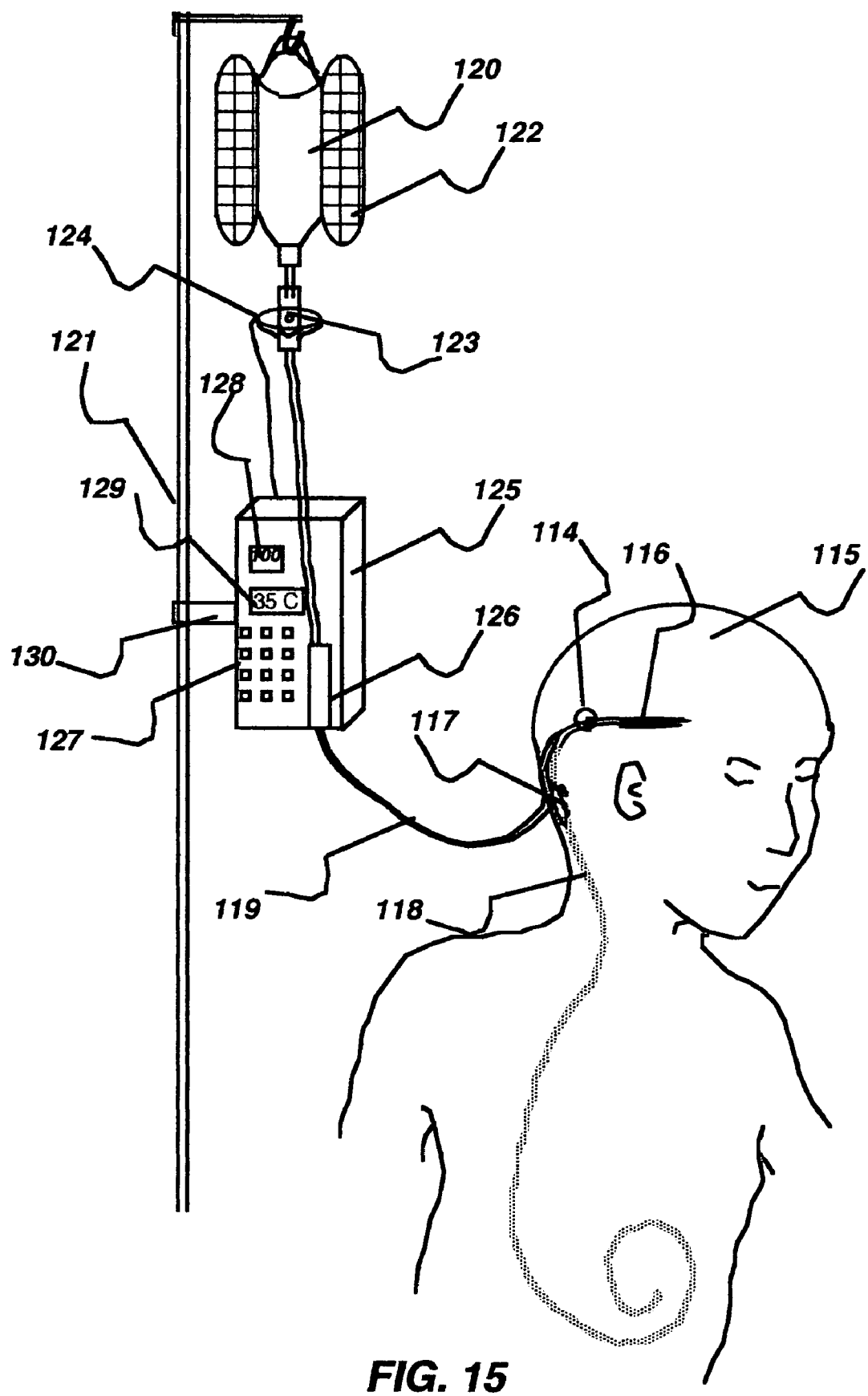
FIG. 15 shows an exemplary setup of the heat exchange procedure using the double barrel catheter in one embodiment of the present invention.

FIG. 15 shows an exemplary setup of the heat exchange procedure using the double barrel catheter in one embodiment of the present invention. The proximal ends of the double barrel catheter 116 protruding from the burr hole 114 are connected to the CSF-flow control valve 117 which in turn is connected to the peritoneal catheter 118. The heat-exchange catheter proximal portion 94 is connected to an infusion system comprising a fluid line 119, containing cooled physiologic solution 120, hanging from an IV stand 121, with ice packs placed around the fluid 122, and dripping into a chamber 123, with volume control 124, and circulated by an infusion pump 125, with safety clamp 126 and selectable delivery rate 127, that could be displayed 128. A temperature sensor could read out 129 the temperature of the physiologic solution. The pump system is suspended by a clamp 130 of the IV stand. The proximal end of the drainage catheter 89 could be connected to a ventriculo-peritoneal 118 or ventriculo-atrial shunting system, providing means of drainage of excess cerebrospinal fluid to maintain the desired intracranial pressure. The rate of drainage of CSF is predetermined by the pressure of the CSF-flow control valve. The CSF flow control valve as disclosed in U.S. Pat. No. 4,552,553 to Schulte et al. and U.S. Pat. No. 4,560,375 to Schulte, et al. has three pressure ranges: low, medium and high. Each valve is individually tested to insure conformance with its labeled pressure/flow characteristics. The outflow rate is a sum total of the inflow rate (from the supply heat exchange catheter) and the estimated CSF production rate (normal, approximately 20 ml/hr). The system provides cooling by infusion of a refrigerated physiological solution, which could also be warmed to body temperature for the rewarming phase. The choice of physiologic solution used for hypothermia could have a profound effect on the viability of nerve tissue, which are particularly vulnerable to hypoxic-ischemia cellular injury as disclosed by Ikonomovic M, Kelly K M, Hentosz T M, et al., in an article entitled "Ultraprofound cerebral hypothermia and blood substitution with an acellular synthetic solution maintains neuronal viability in rat hippocampus", published in Cryo Letters, vol. 22, pp. 19-26, (2001). It is therefore desirable to introduce specifically chosen constituents of physiological solution with the aim of maintaining neuronal viability and reversal of programmed cell death or apoptosis. The level of cooling (cisternohypothermia) or rewarming is dependent on the temperature of the cooling source and the flow rate of the infusion pump.

Figure 16:
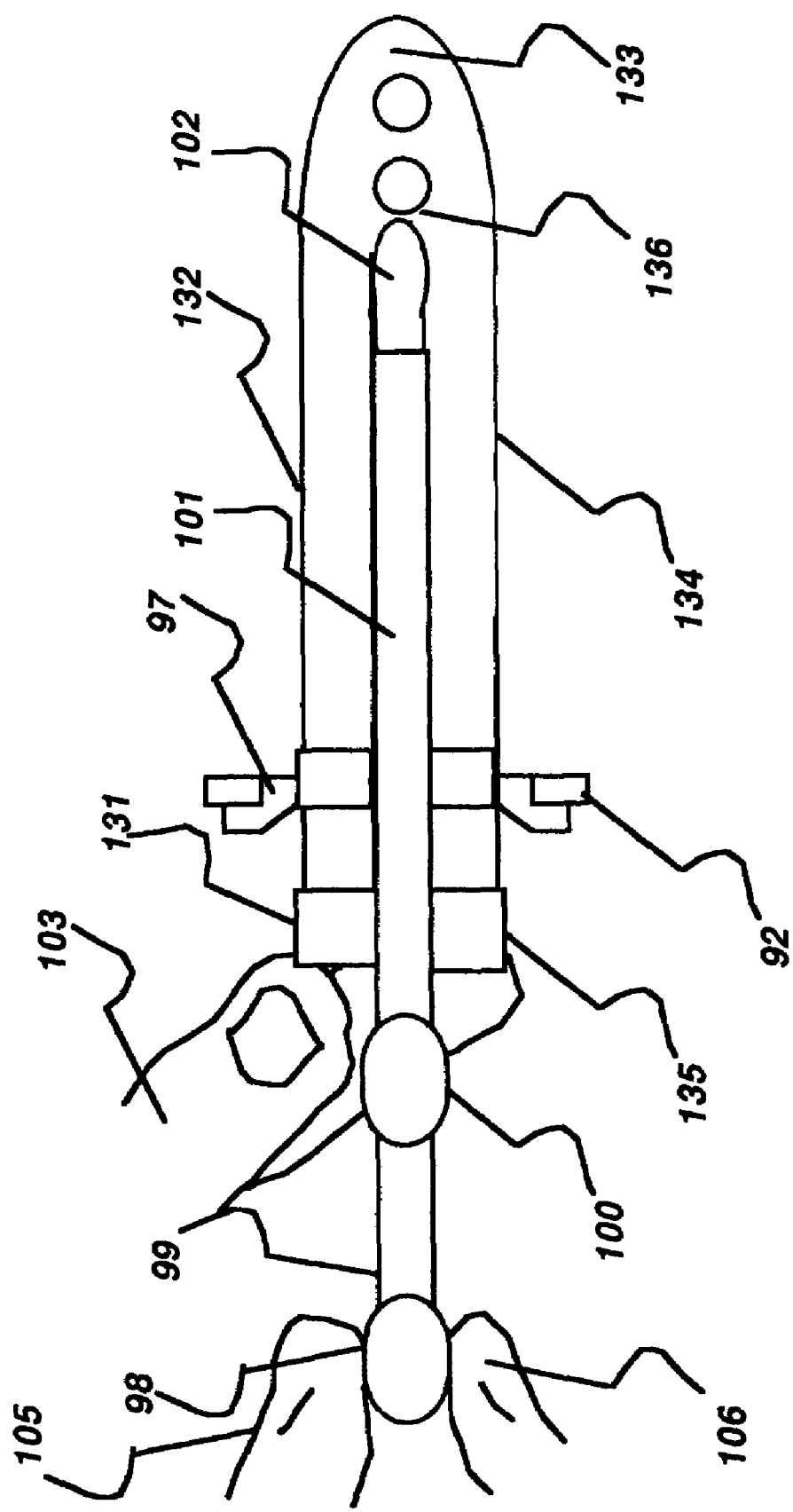
FIG. 16 shows another embodiment of the present invention as a loop catheter for internal cisternohypothermia.

FIG. 16 shows another embodiment of the present invention as a loop catheter for internal cisternohypothermia. For many patients, other than those with brain injury, the introduction of physiologic saline into the CSF ventricles for the purpose of cooling may be unacceptable. Accomplishing cooling of the CSF compartment is still possible using a modification of the present invention. The ventricular catheter used for this purpose is a blind loop, through which heat exchange fluid (that provides cooling—coolant or rewarming) flows at a predetermined rate. The catheter could be made from silicon elastomer tubing impregnated with white barium sulfate to provide radiopacity, similar to that illustrated above (FIG. 10). The catheter has an efferent arm comprising of proximal end 131, which fits to heat exchange fluid source 113, a mid portion 132, a cooling end loop 133 placed in the ventricle, and an afferent arm that returns the solution back to the heat exchange fluid reservoir 113, through its mid portion 134 and proximal end 135 connected to the fluid line. The depth of hypothermia is determined by the temperature of the cooling source and the flow rate of the cooling solution. A middle plate between the two arms of the loop catheter is made of a firm polypropylene base with perforated holes through which the tip of the stainless steel stylet 101 of the catheter introducer could be inserted. The catheter introducer is held between the first 105 and second 106 fingers of one hand at the stylet grip 98, and at the shaft grip 100 between the first 103 and second fingers 104 of the other hand, with the tip of the stainless steel stylet introduced into a perforated hole in the distal portion of the middle plate 136 of the catheter. It is then introduced into the ventricle with the loop 133 end placed at the appropriate level. A quick release action by pulling the stylet grip 98 approximately 1.5 cm back will allow the catheter to be released into the ventricle.

Figure 17:
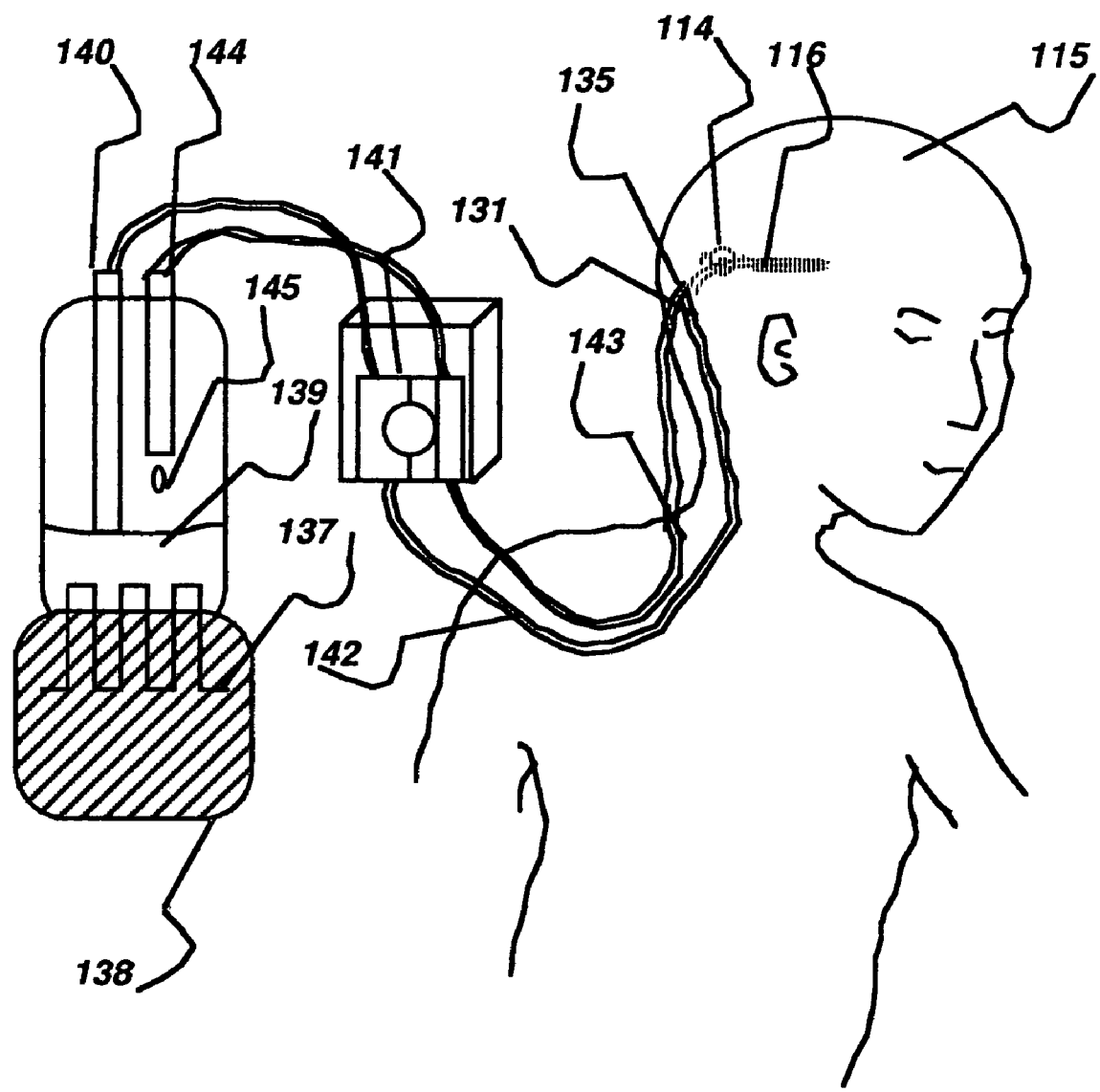
FIG. 17 shows an exemplary setup of the heat exchange procedure using the loop catheter in one embodiment of the present invention.

FIG. 17 shows an exemplary setup of the heat exchange procedure using the loop catheter in one embodiment of the present invention. The cooling solution is drawn from a refrigerated 137 or ice 138 cooled reservoir 139 through a suction pipe 140 by the action of a pump 141 connected to a fluid line 142, which in turn is connected to the proximal end 131 of the efferent arm of the loop catheter 116 placed within the ventricle through a burr hole 114 on the head 115. The cooling fluid circles the loop and returns through its afferent arm 135 and connected fluid line 143, and through the action of the pump 141 returns the solution 145 through the drainage pipe 144 back to the reservoir 139. The repeated cycling of the fluid provides cooling of the CSF in the ventricles by conduction, with the number of cycles per minute dependent on the setting of the pump speed 141. Similarly, rewarming is accomplished using a heated fluid passed through the fluid lines and loop catheter as described. The pump has a selectable flow rate and could be computer controlled through an RS 232 interface. Both the pump and tubing sets that could be modified for this purpose are obtainable at B. Braun Melsungen AG, Melsungen, Germany, by way of example. The depth of cooling is determined by the temperature of fluid reservoir 139 and the flow rate of the cooling solution.

Figure 18:
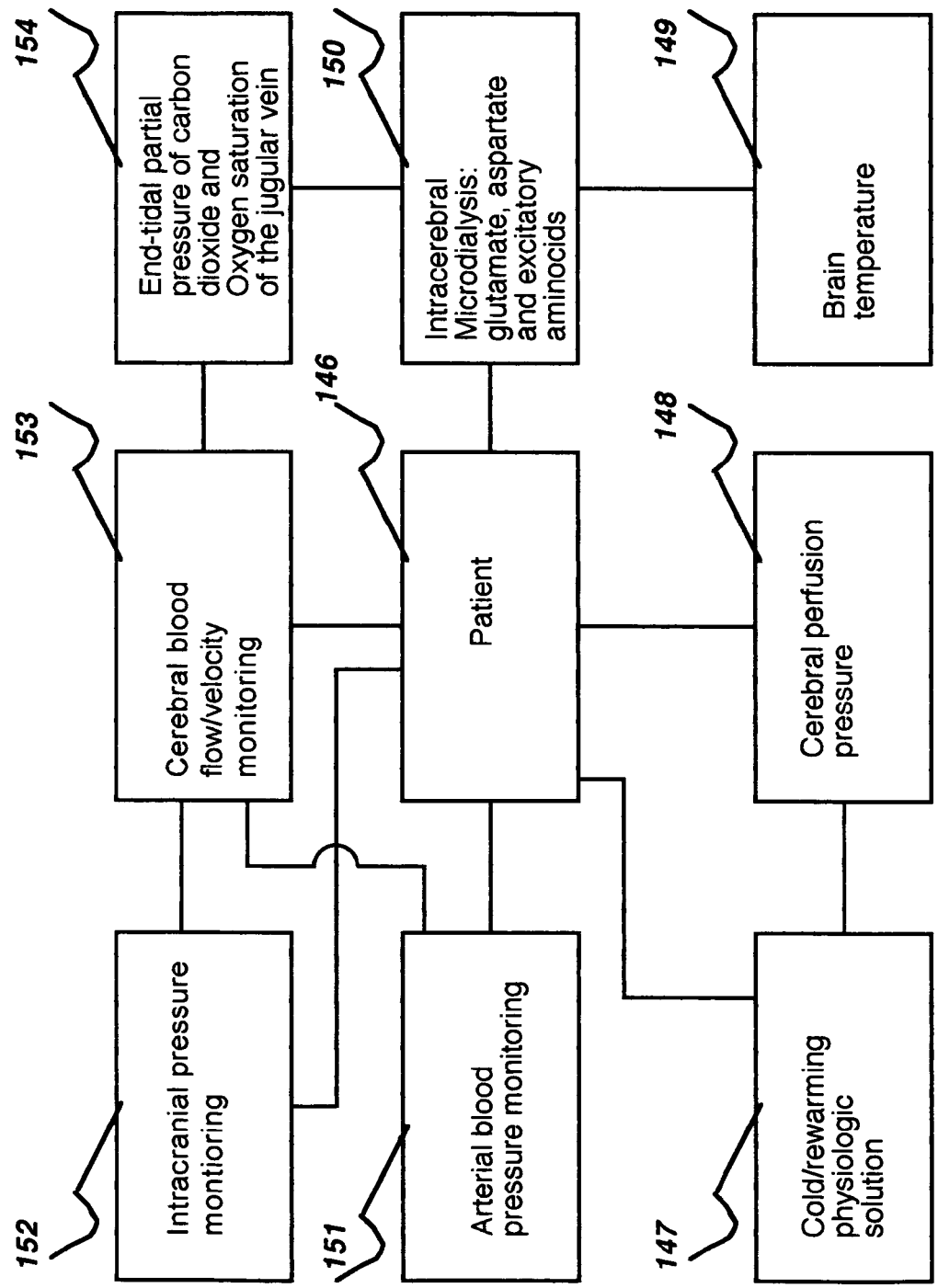
FIG. 18 shows a schematic diagram of interconnected devices in an intensive care setting with the present invention.

FIG. 18 shows a schematic diagram of interconnected devices in an intensive care setting with the present invention. The patient 146 is connected to the device of the present invention for cooling/rewarming 147 of the CSF compartment. The patient is also monitored in an integrated multimodality neurointensive care unit including devices for measurement of cerebral perfusion pressure 148, brain temperature 149, intracerebral microdialysis 150 for measurement of glutamate, aspertate and excitatory amino acids as disclosed by Yamaguchi S, Nakahara K, Miyagi T, et al., in an article entitled "Neurochemical monitoring in the management of severe head injured patients with hypothermia", published in Neurol Res. vol. 22, pp 657-664, (2000), radial arterial blood pressure 151 recording using artery fluid coupled system (for example, pvd, Kirchseeon, Germany), intracranial pressure 152 with intraparenchymal sensor (for example, Camino V420, San Diego, Calif., USA), cerebral blood flow or velocity 153 using a transcranial Doppler device (for example, Multi-Dop T, DWL, Sipplingen, Germany), and end-tidal partial pressure of carbon dioxide 154 using a capnometer (for example, Datex Instrumentarium, Corp., Finland). The data sets are fed into a computer-controlled program.

Figure 19:
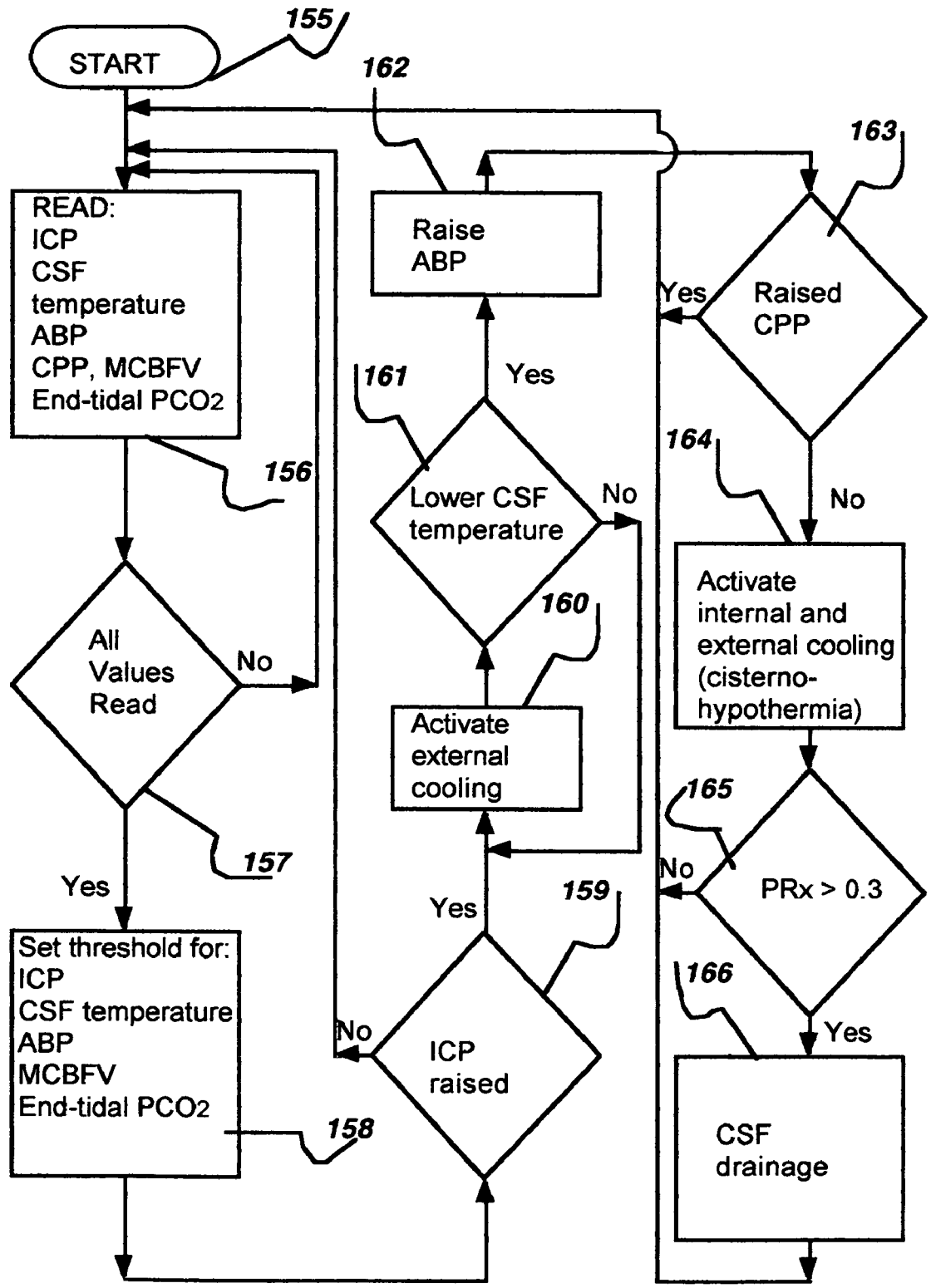
FIG. 19 shows the program flow chart of the invention.

FIG. 19 shows the program flow chart of the invention. The method further includes a system of neurointensive care monitoring devices for providing the physiologic and biochemical indices of brain function. These neurointensive care devices are operatively responsive to set threshold changes and depth of hypothermia. After initialization 155 the microprocessor records the online values 156 of intracranial pressure (ICP), CSF temperature, arterial blood pressure (ABP), cerebral perfusion pressure (CPP), mean cerebral blood flow velocity (MCBFV), oxygen saturation in the jugular vein ($SjO_2$), end-tidal partial pressure of carbon dioxide ($PCO_2$), and intracerebral microdialysis measurement of glutamate, aspartate and excitatory amino acids. All values are read 157, if not, the system proceeds to read all. If all data are read, then the normative data are used to set threshold values 158. The system compares the set threshold for ICP and the online value, if not raised, the system repeats the preceding steps, but if raised 159, the system activates external cooling 160. If the CSF temperature is not lowered to desired level, then the system activates further external cooling 160, but if ICP remains high and the desired level of CPP has not been attained, the system may raise the ABP 162, in order to achieve a raised CPP 163, and if accomplished the system repeats preceding steps. If the optimal cerebral perfusion pressure (CPP-OPT), is not achieved by this measure, the system activates internal cisternohypothermia alongside the external cisternohypothermia 164. The determination of CPP-OPT has been disclosed by Steiner L A, Czosnyka M, Piechnik S K, et al., in an article entitled "Continuous monitoring of cerebrovascular pressure reactivity allows determination of optimal cerebral perfusion pressure in patients with traumatic brain injury", published in Crit Care Med vol. 30, pp. 733-738 (2002). The index PRx is calculated as a moving correlation coefficient of ABP or CPP and ICP as disclosed by Czosnyka M, Smielewski P, Kirkpatrick P, et al. in an article entitled "Continuous assessment of the cerebral vasomotor reactivity in head injury", published in Neurosurgery vol. 41, pp. 11-17 (1997). Based on this and other studies, a PRx value of more than 0.3 indicates impaired cerebrovascular reactivity and a value less than 0.3, intact reactivity as disclosed by Steiner L A, Czosnyka M, Piechnik S K, et al., in an article entitled "Continuous monitoring of cerebrovascular pressure reactivity allows determination of optimal cerebral perfusion pressure in patients with traumatic brain injury", published in Crit Care Med vol. 30, pp. 733-738 (2002). The system determines the PRx, and if greater than 0.3 165, it proceeds to drain the CSF as a means to low the ICP 166.

OTHER PUBLICATIONS

Aaslid R. Cerebral hemodynamics. In: Newell D W et al. (eds.). Transcranial Doppler. Raven Press, New York: p. 49 (1992).

Akisu M, Huseyinov A, Yalaz M, et al. Selective head cooling with hypothermia suppresses the generation of platelet-activating factor in cerebrospinal fluid of newborn infants with perinatal asphyxia. Prostaglandins Leukot Essent Fatty Acids, vol. 69, pp. 45-50, (2003).

Bernard S A, Gray T W, Buist M D, et al. Treatment of comatose survivors of out-of-hospital cardiac arrest with induced hypothermia. N Engl J Med, vol. 346, pp. 557-563 (2002).

Cambria R P, Davison J K, Carter C, et al. Epidural cooling for spinal cord protection during thoracoabdominal aneurysm repair: A five-year experience. J Vasc Surg, vol. 31, pp. 1093-1102, (2000).

Chatauret N, Rose C, Therrien G, Butterworth R F. Mild hypothermia prevents cerebral edema and CSF lactate accumulation in acute liver failure. Metab Brain Dis, vol. 16, pp. 95-102 (2001).

Clifton G L, Miller E R, Choi S C, et al. Lack of effect of induction of hypothermia after acute brain injury. N Engl J Med, vol. 344, pp. 556-563 (2001).

Colbourne F, Sutherland G, Corbett D. Posttraumatic hypothermia: a critical appraisal with implication for clinical treatment. Mol Neurobiol, vol. 14, pp. 171-201 (1997).

Coselli J S, Lemaire S A, Koksoy C, et al. Cerebrospinal fluid drainage reduces paraplegia after thoracoabdominal aortic aneurysm repair: results of a randomized clinical trial. J Vasc Surg, vol. 35, pp. 631-639, (2002).

Czosnyka M. Continuous assessment of the cerebral vasomotor reactivity in head injury. Neurosurgery, vol. 41, pp. 11-17 (1997).

DuBoulay G, O'Connell J, Currie J, et al. Further investigations on pulsatile movements in the cerebrospinal fluid pathway. Acta Radiologica, vol. 13, pp. 496-523 (1972).

Gelfand J A., Dinarello C A, Wolf S M. Fever, including fever of unknown origin. In: Isselbacher K J., et al. (eds.). Harrison's Principles of Internal Medicine. 13th Edition, published by McGraw-Hill Inc., New York: p. 82 (1994).

Gunn A J. Cerebral hypothermia for prevention of brain injury following perinatal asphyxia. Curr Opin Pediatr, vol. 12, 111-115 (2000).

Iida K, Kurisu K, Arita K, Ohtani M. Hyperemia prior to acute brain swelling during rewarming of patients who have been treated with moderate hypothermia for severe head injuries. J Neurosurg, vol. 98, pp. 793-799, (2003).

Ikonomovic M, Kelly K M, Hentosz T M, et al. Ultraprofound cerebral hypothermia and blood substitution with an acellular synthetic solution maintains neuronal viability in rat hippocampus. Cryo Letters, vol. 22, pp. 19-26, (2001).

Inoue S, Kawaguchi M, Kurehara, K, et al. Mild hypothermia can enhance pial arteriolar vasodilatation induced by isoflurane and sevoflurane in cats. Crit Care Med, vol. 30, pp. 1863-1869, (2002).

Irazuzta J E, Olson J, Kiefaber M P, Wong H. Hypothermia decreases excitatory neurotransmitter release in bacterial meningitis in rabbits. Brain Res, vol. 847, pp. 143-148 (1999).

Isikawa T, Marsala M. Hypothermia prevents biphasic glutamate release and corresponding neuronal degeneration after transient spinal cord ischemia in the rat. Cell Mol Neurobiol, vol. 19, pp. 199-208 (1999).

Jiang J, Yu M, Zhu C. Effect of long-term mild hypothermia therapy in patients with severe traumatic brain injury: 1-year follow-up review of 87 cases. J Neurosurg, vol. 93, pp. 546-549 (2000).

Kasza K E, Chen M M. Assessment of impact of advanced energy transmission fluids on district heating and cooling systems (phase I), Argonne National Laboratory, 1987.

Kazemi H, Johnson D C. Regulation of cerebral spinal fluid acid-base balance. J Physiol Rev, vol. 66, pp. 953-1031 (1986).

Kerr E M, Marion D, Sereika M S. The effect of cerebrospinal fluid drainage on cerebral perfusion in traumatic brain injured adults. J Neurosurg Anesthesiol, vol. 12, pp. 324-333 (2000).

Lang E W, Lagopoulos J, Griffith J, et al. Cerebrovascular reactivity testing in head injury: the link between pressure and flow. J Neurol Neurosurg Psychiatry, vol. 74, pp. 1053-1059 (2003).

Metz C, Holzschuh M, Bein T, et al. Moderate hypothermia in patients with severe head injury: cerebral and extracerebral effects. J Neurosurg vol. 85, pp. 533-541 (1996).

Meylaerts S A, De Haan P, Kalkman C J, et al. The influence of regional spinal cord hypothermia on transcranial myogenic motor-evoked potential monitoring and the efficacy of spinal cord ischemia detection. J Thorac Cardiovasc Surg, vol. 118, pp. 1038-1045 (1999).

Meylaerts S A, Kalkman C J, De Haan P, et al. Epidural versus subdural spinal cord cooling: cerebrospinal fluid temperature and pressure changes. Ann Thorac Surg, vol. 70, pp. 222-227, (2000).

Njemanze P C, Beck O J. MR-Gated intracranial CSF dynamics: evaluation of CSF pulsatile flow. AJNR, vol. 10, pp. 77-80 (1989).

Panksepp J. Feeling the pain of social loss. Science, vol. 302, pp. 237-239 (2003).

Piepgras A, Elste V, Frietsch T, Schmiedek P, et al. Effect of moderate hypothermia on experimental severe subarachnoid hemorrhage, as evaluated by apparent diffusion coefficient changes. Neurosurgery, vol. 48, pp. 1128-1134 (2001).

Rosner M. Pathophysiology and management of increased intracranial pressure. In: Andrews B T. (ed.) Neurosurgical intensive care, McGraw Hill Inc., New York: pp. 57-112 (1993).

Schubert A. Side effects of mild hypothermia. J Neurosurg Anesthes vol. 7, 139-147 (1995).

Shiogai T, Nara I, Saruta K, et al. Continuous monitoring of cerebrospinal fluid acid-base balance and oxygen metabolism in patients with severe head injury: pathophysiology and treatments for cerebral acidosis and ischemia. Acta Neurochir Suppl (Wien), vol. 75, pp. 49-55, (1999).

Shiozaki T, Hayakata T, Taneda M, et al. A multicenter prospective randomized controlled trial of the efficacy of mild hypothermia for severely head injured patients with low intracranial pressure. J Neurosurg vol. 94, pp. 50-54 (2001).

Slade J, Kerr M E, Marion D. Effect of therapeutic hypothermia on the incidence and treatment of intracranial hypertension. J Neurosci Nurs, vol. 32, pp. 264-269 (1999).

Steiner L A, Czosnyka M, Piechnik S K, et al. Continuous monitoring of cerebrovascular reactivity allows determination of optimal cerebral perfusion pressure in patients with traumatic brain injury. Crit Care Med vol. 30, pp. 733-738 (2002).

Svensson L G, Khitin L, Nadolny E M, Kimmel W A. Systemic temperature and paralysis after thoracoabdominal and descending aortic operations. Arch Surg, vol. 138, pp. 175-179 (2003).

Trowbridge C, Bruhn T, Arends B. Selective deep spinal hypothermia with vacuum-assisted cerebral spinal fluid drainage for thoracoabdominal aortic surgery. J Extra Corpor Technol, vol. 35, pp. 152-155 (2003).

Wass C T., et al. Temperature changes of .gtoreq.1.degree. C. alter functional neurologic outcome and histopathology in a canine model of complete cerebral ischemia. Anesthesiology, vol. 83, pp. 325-335 (1995).

Yamaguchi S, Nakahara K, Miyagi T, et al. Neurochemical monitoring in the management of severe head injured patients with hypothermia. Neurol Res, vol. 22, pp. 657-664, (2000).

What is claimed is:

1. A method for hypothermia and rewarming of the cerebrospinal fluid in the brain comprising the steps of:
   (a) providing a heat-exchange ventricular catheter;
   (b) simultaneously with (a) providing a drainage ventricular catheter;
   (c) internally implanting the distal ends of the heat exchange and drainage catheters into the cerebral ventricle through a burr hole or twist drill;
   whereby the catheters are placed within the ventricle using ventricular catheter introducers anchored into a slit opening and perforated hole to the distal ends of the catheters respectively, the distal end of the catheter placed above the level of foramen Monro within the ventricle;
   (d) connecting the proximal end of the heat-exchange catheter to an infusion system;
   (e) providing an infusion system containing sterile physiologic solution being at a temperature other than that of the cerebrospinal fluid, wherein a sterile physiologic solution flows in a fluid line into the heat-exchange catheter, the sterile physiologic solution of known chemical constituents, and prepared to preserve cell metabolic energy stores;
   (f) providing an infusion pump programmed to deliver the sterile physiologic solution at a predetermined rate;
   (g) infusing the sterile physiologic solution directly into the cerebral ventricles;
   (h) mixing the sterile physiologic solution with cerebrospinal fluid and altering the temperature of the fluid bathing the regulatory centers in the brain, whereby the sterile physiologic solution mixes with the chemistry of the cerebrospinal fluid bathing the regulatory centers in order to maintain neuronal viability;
   (i) draining excess cerebrospinal fluid through the drainage catheter to maintain the desired intracranial pressure;
   (j) providing pulsatile movement of cerebrospinal fluid to cause heat exchange spreading throughout the brain and spinal cord;
   (k) altering the temperature of cerebrospinal fluid and blood bathing wider brain areas including those involved in regulation of temperature, pain, and emotional stress and further thereby altering central afferents to the neurons in both the preoptic anterior hypothalamus and posterior hypothalamus;
   (l) resetting the body temperature based on the temperature of the cerebrospinal fluid;
   (m) modulating physical pain by promoting antinociceptive response;
   (n) reducing psychological pain by reducing stimulation of periaqueductal gray area of the brain stem;
   (o) reducing intracranial pressure by physical contraction of the cerebrospinal fluid volume in response to hypothermia;
   (p) reducing intracranial pressure and spinal subdural pressure gradients by drainage of excess cerebrospinal fluid;
   (q) improving neuronal cell energy stores by decreasing the cerebral metabolic rate; and
   (r) reducing overall brain temperature by reducing metabolic heat production.

2. The method of claim 1, wherein both the heat-exchange and drainage catheter are made of silicone elastomer tubing.

3. The method of claim 2, wherein the said silicone elastomer tubing is impregnated with barium sulfate to provide radiopacity.

4. The method of claim 3, wherein the said silicone elastomer tubing of the heat exchange and drainage catheters are physically joined together on a firm polypropylene plate to provide rigidity, insulation and resistance to kinking and forming a single catheter with double lumen or double barrel at the proximal, mid and distal portions.

5. The method of claim 4, wherein the said silicone elastomer tubing is graphite-impregnated at points 5, 10, 15 cm from the proximal tip to enable the surgeon to gauge the depth of the penetration of the catheter into the lateral ventricle.

6. The method of claim 5, wherein the said the distal portion of the heat exchange catheter has four slit openings at 90 degrees near the distal end, designed to provide protection from retrograde flow and occlusion of the catheter, and the distal portion of the drainage catheter has perforated holes.

7. The method of claim 6, wherein the heat exchange and drainage catheter joined together forming a double barrel catheter is introduced into the ventricle using a ventricular introducer held between the first and third fingers of one hand like a pair of Chinese chopsticks with the tips inserted into the slit openings and perforated holes and released into the ventricle by a swift action.

8. The method of claim 7, wherein the said proximal portion of the catheters has two right angle clips that are designed to angulate each catheter so that the proximal portion of the heat exchange catheter is turned away from the proximal portion of the drainage catheter.

9. The method of claim 8, wherein the proximal end of the heat exchange catheter is connected to an infusion pump with regulated flow rate of cooling fluid at a set temperature, and the proximal end of the drainage catheter is connected to a cerebrospinal fluid flow control valve attached to an implanted ventriculo-peritoneal or ventriculo-atrial shunting system.

10. The method of claim 9, wherein the depth of hypothermia is determined by the flow rate and temperature of the physiologic solution.

11. The method of claim 10, wherein the depth of hypothermia is monitored by a system of neurointensive care monitoring devices providing the physiologic and biochemical indices of brain function, said neurointensive care devices operatively responsive to set threshold changes in depth of hypothermia and changes in cerebral autoregulation and cerebral vasoreactivity.

12. A method for hypothermia and rewarming of the cerebrospinal fluid in the brain comprising the steps of:
  (a) providing a heat-exchange ventricular catheter folded to form a blind loop at the distal end creating a second catheter;
  (b) simultaneously with (a) providing an afferent arm for inflow of heat exchange fluid;
  (c) simultaneously with (b) providing an efferent arm for outflow of heat exchange fluid;
  (d) providing a proximal end with an inlet and outlet to the catheter lumen through which the heat exchange fluid flows continuously;
  (e) internally implanting the heat exchange loop catheter into the cerebral ventricle through a burr hole or twist drill;
  whereby the afferent and efferent arms of the catheters are placed within the ventricle using ventricular catheter introducers anchored into a slit opening and perforated hole to the distal end of the catheter, and the distal end of the catheter placed above the level of foramen Monro within the ventricle;
  (f) connecting the proximal end of the heat-exchange catheter to an infusion system;
  (g) providing an infusion system containing heat exchange fluid being at a temperature other than that of the cerebrospinal fluid, wherein a heat exchange fluid flows in a fluid line into the heat-exchange loop catheter distal end;
  (h) providing pulsatile movement of cerebrospinal fluid to cause heat exchange spreading throughout the brain and spinal cord;
  (i) altering the temperature of cerebrospinal fluid and blood bathing wider brain areas including those involved in regulation of temperature, pain, and emotional stress and further thereby altering central afferents to the neurons in both the preoptic anterior hypothalamus and posterior hypothalamus;
  (j) resetting the body temperature based on the temperature of the cerebrospinal fluid;
  (k) modulating physical pain by promoting anti-nociceptive response;
  (l) reducing psychological pain by reducing stimulation of periaqueductal gray area of the brain stem;
  (m) reducing intracranial pressure by physical contraction of the cerebrospinal fluid volume in response to hypothermia;
  (n) improving neuronal cell energy stores by decreasing the cerebral metabolic rate; and
  (o) reducing overall brain temperature by reducing metabolic heat production.

13. The method of claim 12, wherein the said blind loop catheter is made of silicone elastomer tubing.

14. The method of claim 13, wherein the said silicone elastomer tubing is impregnated with barium sulfate to provide radiopacity.

15. The method of claim 14, wherein the said silicone elastomer tubing of the catheter has afferent and efferent arms that are physically joined together on a firm polypropylene plate to provide rigidity, insulation and resistance to kinking placed in the middle to form a single continuous catheter with proximal, mid and distal portions ending in a blind loop.

16. The method of claim 15, wherein the said polypropylene plate has perforated holes through which the tip of the ventricular catheter introducer could be inserted.

17. The method of claim 16, wherein the said silicone elastomer tubing is graphite-impregnated at points 5, 10, 15 cm from the proximal tip to enable the surgeon to gauge the depth of the penetration of the catheter into the lateral ventricle.

18. The method of claim 17, wherein the blind loop catheter is introduced into the ventricle using a ventricular introducer held between the first and third fingers of one hand like a pair of Chinese chopsticks with the tips inserted into the perforated holes in the middle plate and released into the ventricle by a swift action.

19. The method of claim 18, wherein the said proximal portion of the catheters has two right angle clips that are designed to angulate each catheter so that the proximal portion of the afferent arm of the catheter is turned away from the proximal portion of the efferent arm of the catheter.

20. The method of claim 19, wherein the proximal end of the afferent arm of the blind loop catheter is connected to an infusion pump with regulated flow rate of cooling fluid at a set temperature, and the proximal end of the catheter is connected to a cerebrospinal fluid flow control valve attached to an implanted ventriculo-peritoneal or ventriculo-atrial shunting system.

* * * * *